United States Patent
Rubin et al.

(10) Patent No.: US 9,090,899 B2
(45) Date of Patent: Jul. 28, 2015

(54) METHODS OF DIAGNOSING AND TREATING PROSTATE CANCER CHARACTERIZED BY NDRG1-ERG FUSION

(75) Inventors: Mark A. Rubin, New York, NY (US); Dorothee Pflueger, Zurich (CH); David S. Rickman, New York, NY (US)

(73) Assignee: CORNELL UNIVERSITY, Ithaca, NY (US)

( * ) Notice: Subject to any disclaimer, the term of this patent is extended or adjusted under 35 U.S.C. 154(b) by 501 days.

(21) Appl. No.: 13/254,071

(22) PCT Filed: Mar. 8, 2010

(86) PCT No.: PCT/US2010/026495
§ 371 (c)(1),
(2), (4) Date: Aug. 31, 2011

(87) PCT Pub. No.: WO2010/102277
PCT Pub. Date: Sep. 10, 2010

(65) Prior Publication Data
US 2012/0039889 A1 Feb. 16, 2012

Related U.S. Application Data

(60) Provisional application No. 61/158,276, filed on Mar. 6, 2009.

(51) Int. Cl.
*C12Q 1/68* (2006.01)
*C12N 15/62* (2006.01)
*C07K 14/47* (2006.01)
*C07K 14/82* (2006.01)
*G01N 33/574* (2006.01)
*A61K 38/00* (2006.01)

(52) U.S. Cl.
CPC .............. *C12N 15/62* (2013.01); *C07K 14/47* (2013.01); *C07K 14/82* (2013.01); *C12Q 1/6886* (2013.01); *G01N 33/57434* (2013.01); *A61K 38/00* (2013.01)

(58) Field of Classification Search
None
See application file for complete search history.

(56) References Cited

U.S. PATENT DOCUMENTS 6,582,908 B2 * 6/2003 Fodor et al. .................. 506/9

OTHER PUBLICATIONS

Kumar-Sinha et al. Nature Reviews Cancer, 2008, vol. 8, pp. 497-511.*

* cited by examiner

*Primary Examiner* — Juliet Switzer
(74) *Attorney, Agent, or Firm* — Scully, Scott, Murphy & Presser, P.C.

(57) ABSTRACT

An in depth analysis of prostate cancer prostatectomy samples which over-express the ERG oncogene led to the discovery of a novel gene translocation in prostate cancer, between the NDRG1 gene (N-myc downstream regulated gene 1) on chromosome 8 and the ERG oncogene on chromosome 21, leading to the expression of a chimeric NDRG1-ERG protein. Methods and compositions useful for diagnosing and treating prostate cancer characterized by NDRG1-ERG fusion are described.

15 Claims, 18 Drawing Sheets

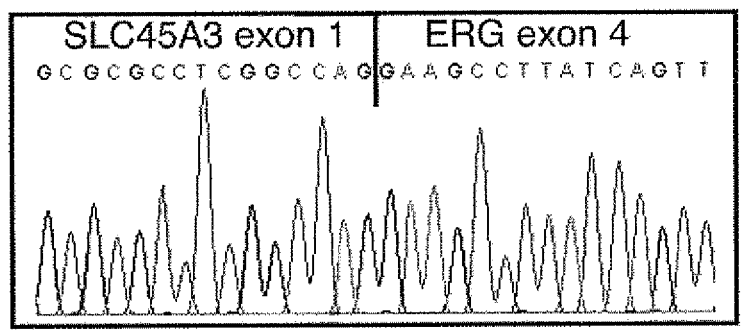
FIGURE 1B

Figure 4A

NDRG1 ex1-3 – ERG ex4-12 (SEQ ID No: 6)

aacaaacctcgcctggctcccagctggtgctgaagctcgtcagttcaccatccgccctcggcttccgcggggcgctgggccgccagcctcggcaccgtcctttcctttctccctcgcgttaggcagg
tgacagcagggacatgtctcgggagatgcaggatgtagacctcgctgaggtgaagcctttggtggagaaaggggagaccatcaccggcctcctgcaagagtttgatgtccagaagcctta
tcagttgtgagtgaggaccagtcgttgtttgagtgtgcctacggaacgccacacctggctaagacagagatgaccgcgtcctcct
ccagcgactatggacagacttccaagatgagcccacgcgtccctcagcaggattggctgtctcaaccccagccagggtcacc
atcaaaatggaatgtaaccctagccaggtgaatggctcaaggaactctcctgatgaatgcagtgtggccaaaggcgggaagat
ggtgggcagcccagacaccgttgggatgaactacggcagctacatggaggagaagcacatgccacccccaaacatgaccac
gaacgagcgcagagttatcgtgccagcagatcctacgctatggagtacagaccatgtgcggcagtggctggagtgggcggtg
aaagaatatggccttccagacgtcaacatcttgttattccagaacatcgatgggaaggaactgtgcaagatgaccaaggacgact
tccagaggctcaccccagctacaacgccgacatcctctctcacatctccactacctcagagagactcctcttccacatttgactt
cagatgatgttgataaagccttacaaaactctccacggttaatgcatgctagaaacacaggggtgcagcttttattttcccaaata
cttcagtatatcctgaagctacgcaaagaattacaactaggccagatttaccatatgagcccccaggagatcagcctggaccgg
tcacggccaccccacgcccagtcgaaagctgctcaaccatctccttccacagtgcccaaaactgaagaccagcgtcctcagtt
agatcctatcagattcttggaccaacaagtagccgccttgcaaatccaggcagtggccagatccagctttggcagttcctcctgg
agctcctgtcggacagctccaactccagctgcatcacctgggaaggcaccaacggggagttcaagatgacggatcccgacga
ggtggcccggcgctggggagagcggaagagcaaacccaacatgaactacgataagctcagccgcgccctccgttactactat
gacaagaacatcatgaccaaggtccatgggaagcgctacgcctacaagttcgacttccacgggatcgcccaggccctccagcc
ccaccccccggagtcatctctgtacaagtaccctcagacctcccgtacatgggctcctatcacgcccacccacagaagatgaa
ctttgtggcgccccaccctccagccctccccgtgacatcttccagtttttttgctgccccaaacccatactggaattcaccaactgg
gggtatatacccaacactaggctccccaccagccatatgccttctcatctgggcacttactactaaagacctggcggaggcttt
cccatcagcgtgcattcaccagcccatcgccacaaactctatcggagaacatgaatcaaaagtgcctcaagaggaatgaaaaaa
gctttactggggctggggaaggaagccggggaagagatccaaagactcttgggaggagttactgaagtcttactacagaaat
gaggaggatgctaaaaatgtcacgaatatggacatatcatctgtggactgaccttgtaaaagacagtgtatgtagaagcatgaagt
cttaaggacaaagtgccaaagaaagtggtcttaagaaatgtataaactttagagtagagtttggaatcccactaatgcaaactggg
atgaaactaaagcaatagaaacaacacagttttgacctaacataccgtttataatgccatttaaggaaaactacctgtatttaaaaat
agaaacatatcaaaaacaagagaaaagacacgagagagactgtggcccatcaacagacgttgatatgcaactgcatggcatgt
gctgttttggttgaaatcaaatacattccgtttgatggacagctgtcagctttctcaaactgtgaagatgacccaaagtttccaactcc
tttacagtattaccgggactatgaactaaaaggtgggactgaggatgtgtatagagtgagcgtgtgattgtagacagaggggtga
agaaggaggaggaagaggcagagaaggaggagaccaggctgggaaagaaacttctcaagcaatgaagactggactcagg
acatttggggactgtgtacaatgagttatggagactcgagggttcatgcagtcagtgttataccaaacccagtgttaggagaaagg
acacagcgtaatggagaaaggggaagtagtagaattcagaaacaaaaatgcgcatctcttcttgtttgtcaaatgaaaattttaact
ggaattgtctgatatttaagagaaacattcaggacctcatcattatgtgggggctttgttctccacagggtcaggtaagagatggcc
ttcttggctgccacaatcagaaatcacgcaggcatttgggtaggcggcctccagtttccttgagtcgcgaacgctgtgcgtttgt
cagaatgaagtatacaagtcaatgttttccccctttttataataattatataacttatgcatttatacactacgagttgatctcggcca
gccaaagacacacgacaaaagagacaatcgatataatgtggccttgaattttaactctgtatgcttaatgtttacaatatgaagttatt
agttcttagaatgcagaatgtatgtaataaaataagcttggcctagcatggcaaatcagatttatacaggagtctgcatttgcactttt
ttagtgactaaagttgcttaatgaaaacatgtgctgaatgttgtggattttgtgttataatttactttgtccaggaacttgtgcaaggga
gagccaaggaaataggatgtttggcaccc

Figure 4B

*Variant 1*: NDRG1 ex1-3 – ERG ex4-12  (SEQ ID No: 7)

MSREMQDVDLAEVKPLVEKGETITGLLQEFDVQEALSVVSEDQSLFECAYGTPH
LAKTEMTASSSSDYGQTSKMSPRVPQQDWLSQPPARVTIKMECNPSQVNGSRNS
PDECSVAKGGKMVGSPDTVGMNYGSYMEEKHMPPPNMTTNERRVIVPADPTL
WSTDHVRQWLEWAVKEYGLPDVNILLFQNIDGKELCKMTKDDFQRLTPSYNAD
ILLSHLHYLRETPLPHLTSDDVDKALQNSPRLMHARNTGGAAFIFPNTSVYPEAT
QRITTRPDLPYEPPRRSAWTGHGHPTPQSKAAQPSPSTVPKTEDQRPQLDPYQILG
PTSSRLANPGSGQIQLWQFLLELLSDSSNSSCITWEGTNGEFKMTDPDEVARRWG
ERKSKPNMNYDKLSRALRYYYDKNIMTKVHGKRYAYKFDFHGIAQALQPHPPE
SSLYKYPSDLPYMGSYHAHPQKMNFVAPHPPALPVTSSSFFAAPNPYWNSPTGGI
YPNTRLPTSHMPSHLGTYY

Figure 5A

NDRG1 ex 1-2 -ERG ex 4-12 Variant 2 : (SEQ ID No: 8)

aacaaacctcgcctggctcccagctggtgctgaagctcgtcagttcaccatccgccctcggcttccgcggggcgctgggccgccagcctcggcaccgtcctttcctttctccctcgcgttaggcagg
tgacagcagggacatgtctcgggagatgcaggatgtagacctcgctgaggtgaagcctttggtggagaaaggggag gaagccttatcagttgtgagtgaggaccagtc
gttgtttgagtgtgcctacggaacgccacacctggctaagacagagatgaccgcgtcctcctccagcgactatggacagacttcc
aagatgagcccacgcgtccctcagcaggattggctgtctcaaccccagccagggtcaccatcaaaatggaatgtaaccctag
ccaggtgaatggctcaaggaactctcctgatgaatgcagtgtggccaaaggcgggaagatggtgggcagcccagacaccgtt
gggatgaactacggcagctacatggaggagaagcacatgccaccccaaacatgaccacgaacgagcgcagagttatcgtg
ccagcagatcctacgctatggagtacagaccatgtgcggcagtggctggagtgggcggtgaaagaatatggccttccagacgt
caacatcttgttattccagaacatcgatggggaaggaactgtgcaagatgaccaaggacgacttccagaggctcaccccagcta
caacgccgacatccttctctcacatctccactacctcagagagactcctcttccacatttgacttcagatgatgttgataaagccttac
aaaactctccacggttaatgcatgctagaaacacagggggtgcagcttttattttcccaaatacttcagtatatcctgaagctacgca
aagaattacaactaggccagatttaccatatgagcccccaggagatcagcctggaccggtcacggccaccccacgcccagt
cgaaagctgctcaaccatctccttccacagtgcccaaaactgaagaccagccgtcctcagttagatccttatcagattcttggacca
acaagtagccgccttgcaaatccaggcagtggccagatccagctttggcagttcctcctggagctcctgtcggacagctccaact
ccagctgcatcacctgggaaggcaccaacggggagttcaagatgacggatcccgacgaggtggcccggcgctggggagag
cggaagagcaaacccaacatgaactacgataagctcagccgcgccctccgttactactatgacaagaacatcatgaccaaggt
ccatgggaagcgctacgcctacaagttcgacttccacgggatcgcccaggccctccagccccaccccccggagtcatctctgt
acaagtaccctcagacctcccgtacatgggctcctatcacgcccacccacagaagatgaactttgtggcgccccaccctccag
ccctccccgtgacatcttccagttttttgctgccccaaacccatactggaattcaccaactgggggtatataccccaacactaggc
tccccaccagccatatgccttctcatctgggcacttactactaaagacctggcggaggcttttcccatcagcgtgcattcaccagc
ccatcgccacaaactctatcggagaacatgaatcaaaagtgcctcaagaggaatgaaaaaagctttactggggctggggaagg
aagccggggaagagatccaaagactcttggaggagttactgaagtcttactacagaaatgaggaggatgctaaaaatgtca
cgaatatggacatatcatctgtggactgaccttgtaaaagacagtgtatgtagaagcatgaagtcttaaggacaaagtgccaaag
aaagtggtcttaagaaatgtataaacttagagtagagtttggaatcccactaatgcaaactgggatgaaactaaagcaatagaaa
caacacagttttgacctaacataccgtttataatgccattttaaggaaaactacctgtatttaaaaatagaaacatatcaaaaacaag
agaaaagacacgagagagactgtggcccatcaacagacgttgatatgcaactgcatggcatgtgctgttttggttgaaatcaaat
acattccgtttgatggacagctgtcagctttctcaaactgtgaagatgacccaaagtttccaactcctttacagtattaccgggactat
gaactaaaaggtgggggactgaggatgtgtatagagtgagcgtgtgattgtagacagaggggtgaagaaggaggaggaagagg
cagagaaggaggagaccaggctgggaaagaaacttctcaagcaatgaagactggactcaggacatttggggactgtgtacaat
gagttatggagactcgagggttcatgcagtcagtgttataccaaacccagtgttaggagaaaggacacagcgtaatggagaaag
ggaagtagtagaattcagaaacaaaatgcgcatctctttcttgtttgtcaaatgaaaattttaactggaattgtctgatatttaagag
aaacattcaggacctcatcattatgtggggctttgttctccacagggtcaggtaagagatggccttcttggctgccacaatcaga
aatcacgcaggcatttgggtaggcggcctccagtttccttgagtcgcgaacgctgtgcgtttgtcagaatgaagtatacaagtc
aatgttttccccctttttatataataattatataacttatgcatttatacactacgagttgatctcggccagccaaagacacacgacaaa
agagacaatcgatataatgtggccttgaattttaactctgtatgcttaatgtttacaatatgaagttattagttcttagaatgcagaatgt
atgtaataaaataagcttggcctagcatggcaaatcagatttatacaggagtctgcatttgcactttttagtgactaaagttgcttaa
tgaaaacatgtgctgaatgttgtggattttgtgttataatttactttgtccaggaacttgtcaagggagagccaaggaaataggatg
tttggcaccc

Figure 5B

*Variant 2*: NDRG1 ex 1-2 - ERG ex 4-12 (SEQ ID No: 9)

MSREMQDVDLAEVKPLVEKGEEALSVVSEDQSLFECAYGTPHLAKTEMTASSSS
DYGQTSKMSPRVPQQDWLSQPPARVTIKMECNPSQVNGSRNSPDECSVAKGGK
MVGSPDTVGMNYGSYMEEKHMPPPNMTTNERRVIVPADPTLWSTDHVRQWLE
WAVKEYGLPDVNILLFQNIDGKELCKMTKDDFQRLTPSYNADILLSHLHYLRETP
LPHLTSDDVDKALQNSPRLMHARNTGGAAFIFPNTSVYPEATQRITTRPDLPYEP
PRRSAWTGHGHPTPQSKAAQPSPSTVPKTEDQRPQLDPYQILGPTSSRLANPGSG
QIQLWQFLLELLSDSSNSSCITWEGTNGEFKMTDPDEVARRWGERKSKPNMNYD
KLSRALRYYYDKNIMTKVHGKRYAYKFDFHGIAQALQPHPPESSLYKYPSDLPY
MGSYHAHPQKMNFVAPHPPALPVTSSSFFAAPNPYWNSPTGGIYPNTRLPTSHM
PSHLGTYY

Figure 10. NDRG1-ERG mRNA over-expression in different cell lines

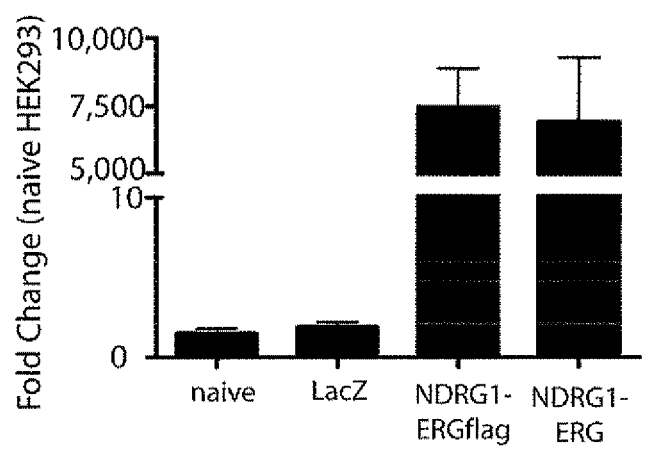
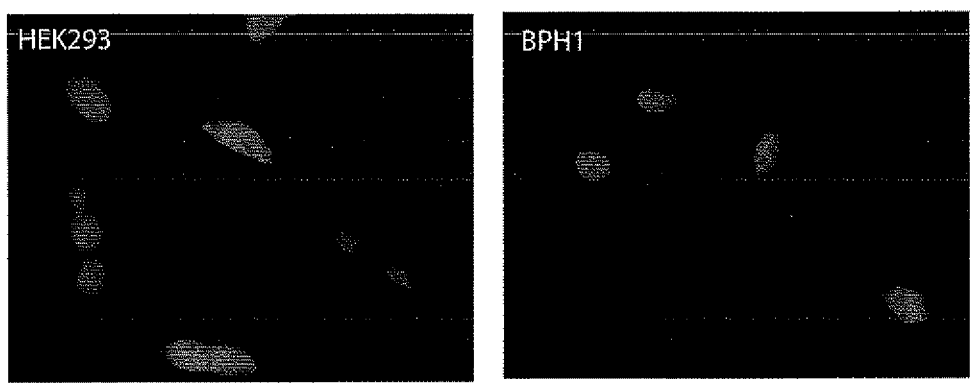
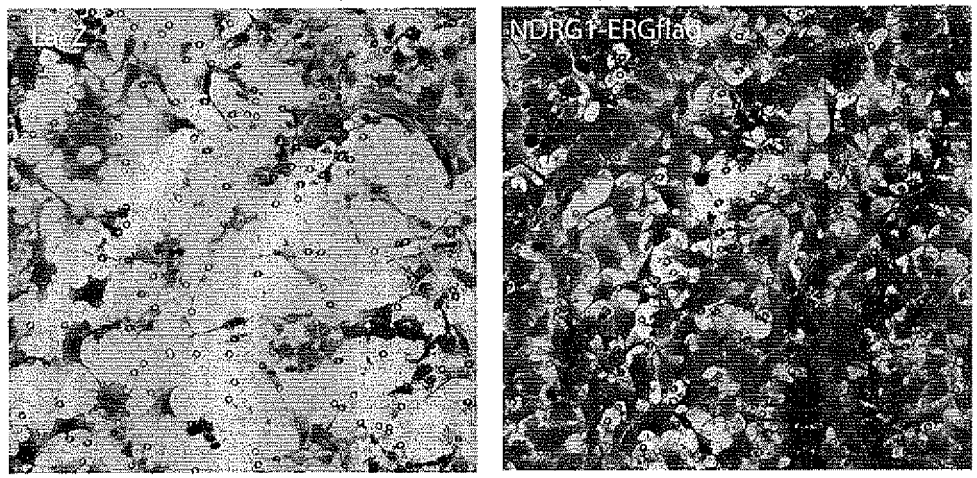
FIGURE 11

SEQUENCE LISTING

<160> NUMBER OF SEQ ID NOS: 58

<210> SEQ ID NO 1
<211> LENGTH: 3123
<212> TYPE: DNA
<213> ORGANISM: Homo sapiens
<220> FEATURE:
<221> NAME/KEY: misc_feature
<222> LOCATION: (1)..(171)
<223> OTHER INFORMATION: Exon 1
<220> FEATURE:
<221> NAME/KEY: misc_feature
<222> LOCATION: (172)..(252)
<223> OTHER INFORMATION: Exon 2
<220> FEATURE:
<221> NAME/KEY: CDS
<222> LOCATION: (190)..(1374)
<220> FEATURE:
<221> NAME/KEY: misc_feature
<222> LOCATION: (253)..(288)
<223> OTHER INFORMATION: Exon 3
<220> FEATURE:
<221> NAME/KEY: misc_feature
<222> LOCATION: (289)..(394)
<223> OTHER INFORMATION: Exon 4
<220> FEATURE:
<221> NAME/KEY: misc_feature
<222> LOCATION: (395)..(515)
<223> OTHER INFORMATION: Exon 5
<220> FEATURE:
<221> NAME/KEY: misc_feature
<222> LOCATION: (516)..(578)
<223> OTHER INFORMATION: Exon 6
<220> FEATURE:
<221> NAME/KEY: misc_feature
<222> LOCATION: (579)..(639)
<223> OTHER INFORMATION: Exon 7
<220> FEATURE:
<221> NAME/KEY: misc_feature
<222> LOCATION: (640)..(726)
<223> OTHER INFORMATION: Exon 8
<220> FEATURE:
<221> NAME/KEY: misc_feature
<222> LOCATION: (727)..(783)
<223> OTHER INFORMATION: Exon 9
<220> FEATURE:
<221> NAME/KEY: misc_feature
<222> LOCATION: (784)..(887)
<223> OTHER INFORMATION: Exon 10
<220> FEATURE:
<221> NAME/KEY: misc_feature
<222> LOCATION: (888)..(944)
<223> OTHER INFORMATION: Exon 11
<220> FEATURE:
<221> NAME/KEY: misc_feature
<222> LOCATION: (945)..(996)
<223> OTHER INFORMATION: Exon 12
<220> FEATURE:
<221> NAME/KEY: misc_feature
<222> LOCATION: (997)..(1044)
<223> OTHER INFORMATION: Exon 13
<220> FEATURE:
<221> NAME/KEY: misc_feature
<222> LOCATION: (1045)..(1080)
<223> OTHER INFORMATION: Exon 14
<220> FEATURE:
<221> NAME/KEY: misc_feature
<222> LOCATION: (1081)..(1132)
<223> OTHER INFORMATION: Exon 15
<220> FEATURE:
<221> NAME/KEY: misc_feature
<222> LOCATION: (1133)..(3081)
<223> OTHER INFORMATION: Exon 16
<220> FEATURE:
<221> NAME/KEY: misc_feature
<222> LOCATION: (3058)..(3063)
<223> OTHER INFORMATION: PolyA signal
<220> FEATURE:

-continued

```
<221> NAME/KEY: misc_feature
<222> LOCATION: (3081)..(3081)
<223> OTHER INFORMATION: PolyA site

<400> SEQUENCE: 1 gcggggcgg ggccgcggcg cctataaagt cgccctccgc ccggacgtaa acaaacctcg      60
cctggctccc agctggtgct gaagctcgtc agttcaccat ccgccctcgg cttccgcggg   120
gcgctgggcc gccagcctcg gcaccgtcct ttcctttctc cctcgcgtta ggcaggtgac   180 agcagggac atg tct cgg gag atg cag gat gta gac ctc gct gag gtg aag   231
          Met Ser Arg Glu Met Gln Asp Val Asp Leu Ala Glu Val Lys
                1               5                  10 cct ttg gtg gag aaa ggg gag acc atc acc ggc ctc ctg caa gag ttt     279
Pro Leu Val Glu Lys Gly Glu Thr Ile Thr Gly Leu Leu Gln Glu Phe
15                  20                  25                  30 gat gtc cag gag cag gac atc gag act tta cat ggc tct gtt cac gtc     327
Asp Val Gln Glu Gln Asp Ile Glu Thr Leu His Gly Ser Val His Val
                35                  40                  45 acg ctg tgt ggg act ccc aag gga aac cgg cct gtc atc ctc acc tac     375
Thr Leu Cys Gly Thr Pro Lys Gly Asn Arg Pro Val Ile Leu Thr Tyr
    50                  55                  60 cat gac atc ggc atg aac cac aaa acc tgc tac aac ccc ctc ttc aac     423
His Asp Ile Gly Met Asn His Lys Thr Cys Tyr Asn Pro Leu Phe Asn
65                  70                  75 tac gag gac atg cag gag atc acc cag cac ttt gcc gtc tgc cac gtg     471
Tyr Glu Asp Met Gln Glu Ile Thr Gln His Phe Ala Val Cys His Val
                80                  85                  90 gac gcc cct ggc cag cag gac ggc gca gcc tcc ttc ccc gca ggg tac     519
Asp Ala Pro Gly Gln Gln Asp Gly Ala Ala Ser Phe Pro Ala Gly Tyr
95                  100                 105                 110 atg tac ccc tcc atg gat cag ctg gct gaa atg ctt cct gga gtc ctt     567
Met Tyr Pro Ser Met Asp Gln Leu Ala Glu Met Leu Pro Gly Val Leu
                115                 120                 125 caa cag ttt ggg ctg aaa agc att att ggc atg gga aca gga gca ggc     615
Gln Gln Phe Gly Leu Lys Ser Ile Ile Gly Met Gly Thr Gly Ala Gly
        130                 135                 140 gcc tac atc cta act cga ttt gct cta aac aac cct gag atg gtg gag     663
Ala Tyr Ile Leu Thr Arg Phe Ala Leu Asn Asn Pro Glu Met Val Glu
            145                 150                 155 ggc ctt gtc ctt atc aac gtg aac cct tgt gcg gaa ggc tgg atg gac     711
Gly Leu Val Leu Ile Asn Val Asn Pro Cys Ala Glu Gly Trp Met Asp
160                 165                 170 tgg gcc gcc tcc aag atc tca gga tgg acc caa gct ctg ccg gac atg     759
Trp Ala Ala Ser Lys Ile Ser Gly Trp Thr Gln Ala Leu Pro Asp Met
175                 180                 185                 190 gtg gtg tcc cac ctt ttt ggg aag gaa gaa atg cag agt aac gtg gaa     807
Val Val Ser His Leu Phe Gly Lys Glu Glu Met Gln Ser Asn Val Glu
                195                 200                 205 gtg gtc cac acc tac cgc cag cac att gtg aat gac atg aac ccc ggc     855
Val Val His Thr Tyr Arg Gln His Ile Val Asn Asp Met Asn Pro Gly
            210                 215                 220 aac ctg cac ctg ttc atc aat gcc tac aac agc cgg cgc gac ctg gag     903
Asn Leu His Leu Phe Ile Asn Ala Tyr Asn Ser Arg Arg Asp Leu Glu
        225                 230                 235 att gag cga cca atg ccg gga acc cac aca gtc acc ctg cag tgc cct     951
Ile Glu Arg Pro Met Pro Gly Thr His Thr Val Thr Leu Gln Cys Pro
240                 245                 250 gct ctg ttg gtg gtt ggg gac agc tcg cct gca gtg gat gcc gtg gtg     999
Ala Leu Leu Val Val Gly Asp Ser Ser Pro Ala Val Asp Ala Val Val
255                 260                 265                 270
```

| | | | | | | | | | | | | | | | |
|---|---|---|---|---|---|---|---|---|---|---|---|---|---|---|---|
| gag | tgc | aac | tca | aaa | ttg | gac | cca | aca | aag | acc | act | ctc | ctc | aag | atg | 1047 |
| Glu | Cys | Asn | Ser | Lys | Leu | Asp | Pro | Thr | Lys | Thr | Thr | Leu | Leu | Lys | Met |
| | | | 275 | | | | | 280 | | | | | | 285 | |

| | | | | | | | | | | | | | | | |
|---|---|---|---|---|---|---|---|---|---|---|---|---|---|---|---|
| gcg | gac | tgt | ggc | ggc | ctc | ccg | cag | atc | tcc | cag | ccg | gcc | aag | ctc | gct | 1095 |
| Ala | Asp | Cys | Gly | Gly | Leu | Pro | Gln | Ile | Ser | Gln | Pro | Ala | Lys | Leu | Ala |
| | | 290 | | | | | 295 | | | | | 300 | | | |

| | | | | | | | | | | | | | | | |
|---|---|---|---|---|---|---|---|---|---|---|---|---|---|---|---|
| gag | gcc | ttc | aag | tac | ttc | gtg | cag | ggc | atg | gga | tac | atg | ccc | tcg | gct | 1143 |
| Glu | Ala | Phe | Lys | Tyr | Phe | Val | Gln | Gly | Met | Gly | Tyr | Met | Pro | Ser | Ala |
| | 305 | | | | | 310 | | | | | 315 | | | | |

| | | | | | | | | | | | | | | | |
|---|---|---|---|---|---|---|---|---|---|---|---|---|---|---|---|
| agc | atg | acc | cgc | ctg | atg | cgg | tcc | cgc | aca | gcc | tct | ggt | tcc | agc | gtc | 1191 |
| Ser | Met | Thr | Arg | Leu | Met | Arg | Ser | Arg | Thr | Ala | Ser | Gly | Ser | Ser | Val |
| 320 | | | | | 325 | | | | | 330 | | | | | |

| | | | | | | | | | | | | | | | |
|---|---|---|---|---|---|---|---|---|---|---|---|---|---|---|---|
| act | tct | ctg | gat | ggc | acc | cgc | agc | cgc | tcc | cac | acc | agc | gag | ggc | acc | 1239 |
| Thr | Ser | Leu | Asp | Gly | Thr | Arg | Ser | Arg | Ser | His | Thr | Ser | Glu | Gly | Thr |
| 335 | | | | 340 | | | | | 345 | | | | | 350 | |

| | | | | | | | | | | | | | | | |
|---|---|---|---|---|---|---|---|---|---|---|---|---|---|---|---|
| cga | agc | cgc | tcc | cac | acc | agc | gag | ggc | acc | cgc | agc | cgc | tcg | cac | acc | 1287 |
| Arg | Ser | Arg | Ser | His | Thr | Ser | Glu | Gly | Thr | Arg | Ser | Arg | Ser | His | Thr |
| | | | | 355 | | | | | 360 | | | | | 365 | |

| | | | | | | | | | | | | | | | |
|---|---|---|---|---|---|---|---|---|---|---|---|---|---|---|---|
| agc | gag | ggg | gcc | cac | ctg | gac | atc | acc | ccc | aac | tcg | ggt | gct | gct | ggg | 1335 |
| Ser | Glu | Gly | Ala | His | Leu | Asp | Ile | Thr | Pro | Asn | Ser | Gly | Ala | Ala | Gly |
| | | | 370 | | | | | 375 | | | | | 380 | | |

| | | | | | | | | | | | | |
|---|---|---|---|---|---|---|---|---|---|---|---|---|
| aac | agc | gcc | ggg | ccc | aag | tcc | atg | gag | gtc | tcc | tgc | tag | gcggcctgcc | 1384 |
| Asn | Ser | Ala | Gly | Pro | Lys | Ser | Met | Glu | Val | Ser | Cys | | |
| | 385 | | | | | 390 | | | | | | | |

| | | |
|---|---|---|
| cagctgccgc | ccccggactc | tgatctctgt | agtggccccc | tcctcccggg | cccctttccg | 1444 |
| ccccctgcct | gccatactgc | gcctaactcg | gtattaatcc | aaagcttatt | ttgtaagagt | 1504 |
| gagctctggt | ggagacaaat | gaggtctatt | acgtgggtgc | cctctccaaa | ggcggggtgg | 1564 |
| cggtggacca | aaggaaggaa | gcaagcatct | ccgcatcgca | tcctcttcca | ttaaccagtg | 1624 |
| gccggttgcc | actctcctcc | cctccctcag | agacaccaaa | ctgccaaaaa | caagacgcgt | 1684 |
| agcagcacac | acttcacaaa | gccaagccta | ggccgccctg | agcatcctgg | ttcaaacggg | 1744 |
| tgcctggtca | aaggccagc | cgcccacttc | ccgtttcctc | tttaactgag | gagaagctga | 1804 |
| tccagttttcc | ggaaacaaaa | tccttttctc | atttggggag | ggggtaata | gtgacatgca | 1864 |
| ggcacctctt | ttaaacaggc | aaaacaggaa | ggggaaaag | gtgggattca | tgtcgaggct | 1924 |
| agaggcattt | ggaacaacaa | atctacgtag | ttaacttgaa | gaaaccgatt | tttaaagttg | 1984 |
| gtgcatctag | aaagctttga | atgcagaagc | aaacaagctt | gatttttcta | gcatcctctt | 2044 |
| aatgtgcagc | aaaagcaggc | gacaaaatct | cctggcttta | cagacaaaaa | tatttcagca | 2104 |
| aacgttgggc | atcatggttt | tgaaggctt | tagttctgct | ttctgcctct | cctccacagc | 2164 |
| cccaacctcc | caccctgat | acatgagcca | gtgattattc | ttgttcaggg | agaagatcat | 2224 |
| ttagatttgt | tttgcattcc | ttagaatgga | gggcaacatt | ccacagctgc | cctggctgtg | 2284 |
| atgagtgtcc | ttgcaggggc | cggagtagga | gcactggggt | ggggggtggaa | ttggggttac | 2344 |
| tcgatgtaag | ggattccttg | ttgttgtgtt | gagatccagt | gcagttgtga | tttctgtgga | 2404 |
| tcccagcttg | gttccaggaa | ttttgtgtga | ttggcttaaa | tccagttttc | aatcttcgac | 2464 |
| agctgggctg | gaacgtgaac | tcagtagctg | aacctgtctg | acccggtcac | gttcttggat | 2524 |
| cctcagaact | ctttgctctt | gtcggggtgg | gggtgggaac | tcacgtgggg | agcggtggct | 2584 |
| gagaaaatgt | aaggattctg | gaatacatat | tccatgggac | tttccttccc | tctcctgctt | 2644 |
| cctcttttcc | tgctccctaa | cctttcgccg | aatgggcag | caccactgac | gtttctgggc | 2704 |
| ggccagtgcg | gctgccaggt | tcctgtacta | ctgccttgta | cttttcattt | tggctcaccg | 2764 |

| | |
|---|---:|
| tggattttct cataggaagt ttggtcagag tgaattgaat attgtaagtc agccactggg | 2824 |
| acccgaggat ttctgggacc ccgcagttgg gaggaggaag tagtccagcc ttccaggtgg | 2884 |
| cgtgagaggc aatgactcgt tacctgccgc ccatcacctt ggaggccttc cctggccttg | 2944 |
| agtagaaaag tcggggatcg gggcaagaga ggctgagtac ggatgggaaa ctattgtgca | 3004 |
| caagtctttc cagaggagtt tcttaatgag atatttgtat ttatttccag accaataaat | 3064 |
| ttgtaacttt gcagcggaaa aaaaaaaaa aaaaaaaaa aaaaaaaaa aaaaaaaa | 3123 |

```
<210> SEQ ID NO 2
<211> LENGTH: 5042
<212> TYPE: DNA
<213> ORGANISM: Homo sapiens
<220> FEATURE:
<221> NAME/KEY: misc_feature
<222> LOCATION: (1)..(119)
<223> OTHER INFORMATION: Exon 1
<220> FEATURE:
<221> NAME/KEY: misc_feature
<222> LOCATION: (120)..(225)
<223> OTHER INFORMATION: Exon 2
<220> FEATURE:
<221> NAME/KEY: misc_feature
<222> LOCATION: (226)..(309)
<223> OTHER INFORMATION: Exon 3
<220> FEATURE:
<221> NAME/KEY: CDS
<222> LOCATION: (273)..(1661)
<220> FEATURE:
<221> NAME/KEY: misc_feature
<222> LOCATION: (310)..(529)
<223> OTHER INFORMATION: Exon 4
<220> FEATURE:
<221> NAME/KEY: misc_feature
<222> LOCATION: (530)..(681)
<223> OTHER INFORMATION: Exon 5
<220> FEATURE:
<221> NAME/KEY: misc_feature
<222> LOCATION: (682)..(885)
<223> OTHER INFORMATION: Exon 6
<220> FEATURE:
<221> NAME/KEY: misc_feature
<222> LOCATION: (886)..(966)
<223> OTHER INFORMATION: Exon 7
<220> FEATURE:
<221> NAME/KEY: misc_feature
<222> LOCATION: (967)..(1038)
<223> OTHER INFORMATION: Exon 8
<220> FEATURE:
<221> NAME/KEY: misc_feature
<222> LOCATION: (1039)..(1107)
<223> OTHER INFORMATION: Exon 9
<220> FEATURE:
<221> NAME/KEY: misc_feature
<222> LOCATION: (1108)..(1164)
<223> OTHER INFORMATION: Exon 10
<220> FEATURE:
<221> NAME/KEY: misc_feature
<222> LOCATION: (1165)..(1212)
<223> OTHER INFORMATION: Exon 11
<220> FEATURE:
<221> NAME/KEY: misc_feature
<222> LOCATION: (1213)..(5109)
<223> OTHER INFORMATION: Exon 12

<400> SEQUENCE: 2
```

| | |
|---|---:|
| gttttcactt ggtcggaatg gggagagtgt gcaagagatc gctgcgggac aggttcctag | 60 |
| agatcgctcc gggacggtcg tgacggcccc cgagggacat gagagaagag gagcggcgct | 120 |
| caggttattc caggatcttt ggagacccga ggaaagccgt gttgaccaaa agcaagacaa | 180 |
| atgactcaca gagaaaaaag atggcagaac caagggcaac taaagccgtc aggttctgaa | 240 |

-continued

| | |
|---|---|
| cagctggtag atgggctggc ttactgaagg ac atg att cag act gtc ccg gac<br>                                                                                   Met Ile Gln Thr Val Pro Asp<br>                                                                                    1                   5 | 293 |
| cca gca gct cat atc aag gaa gcc tta tca gtt gtg agt gag gac cag<br>Pro Ala Ala His Ile Lys Glu Ala Leu Ser Val Val Ser Glu Asp Gln<br>          10                   15                        20 | 341 |
| tcg ttg ttt gag tgt gcc tac gga acg cca cac ctg gct aag aca gag<br>Ser Leu Phe Glu Cys Ala Tyr Gly Thr Pro His Leu Ala Lys Thr Glu<br> 25                   30                       35 | 389 |
| atg acc gcg tcc tcc tcc agc gac tat gga cag act tcc aag atg agc<br>Met Thr Ala Ser Ser Ser Ser Asp Tyr Gly Gln Thr Ser Lys Met Ser<br>40                     45                       50                    55 | 437 |
| cca cgc gtc cct cag cag gat tgg ctg tct caa ccc cca gcc agg gtc<br>Pro Arg Val Pro Gln Gln Asp Trp Leu Ser Gln Pro Pro Ala Arg Val<br>               60                       65                       70 | 485 |
| acc atc aaa atg gaa tgt aac cct agc cag gtg aat ggc tca agg aac<br>Thr Ile Lys Met Glu Cys Asn Pro Ser Gln Val Asn Gly Ser Arg Asn<br>                    75                       80                    85 | 533 |
| tct cct gat gaa tgc agt gtg gcc aaa ggc ggg aag atg gtg ggc agc<br>Ser Pro Asp Glu Cys Ser Val Ala Lys Gly Gly Lys Met Val Gly Ser<br>          90                       95                       100 | 581 |
| cca gac acc gtt ggg atg aac tac ggc agc tac atg gag gag aag cac<br>Pro Asp Thr Val Gly Met Asn Tyr Gly Ser Tyr Met Glu Glu Lys His<br>105                   110                     115 | 629 |
| atg cca ccc cca aac atg acc acg aac gag cgc aga gtt atc gtg cca<br>Met Pro Pro Pro Asn Met Thr Thr Asn Glu Arg Arg Val Ile Val Pro<br>120                   125                  130                135 | 677 |
| gca gat cct acg cta tgg agt aca gac cat gtg cgg cag tgg ctg gag<br>Ala Asp Pro Thr Leu Trp Ser Thr Asp His Val Arg Gln Trp Leu Glu<br>               140                   145                150 | 725 |
| tgg gcg gtg aaa gaa tat ggc ctt cca gac gtc aac atc ttg tta ttc<br>Trp Ala Val Lys Glu Tyr Gly Leu Pro Asp Val Asn Ile Leu Leu Phe<br>             155                   160                165 | 773 |
| cag aac atc gat ggg aag gaa ctg tgc aag atg acc aag gac gac ttc<br>Gln Asn Ile Asp Gly Lys Glu Leu Cys Lys Met Thr Lys Asp Asp Phe<br>         170                   175                  180 | 821 |
| cag agg ctc acc ccc agc tac aac gcc gac atc ctt ctc tca cat ctc<br>Gln Arg Leu Thr Pro Ser Tyr Asn Ala Asp Ile Leu Leu Ser His Leu<br>185                   190                     195 | 869 |
| cac tac ctc aga gag act cct ctt cca cat ttg act tca gat gat gtt<br>His Tyr Leu Arg Glu Thr Pro Leu Pro His Leu Thr Ser Asp Asp Val<br>200                   205                  210                215 | 917 |
| gat aaa gcc tta caa aac tct cca cgg tta atg cat gct aga aac aca<br>Asp Lys Ala Leu Gln Asn Ser Pro Arg Leu Met His Ala Arg Asn Thr<br>             220                   225                  230 | 965 |
| gat tta cca tat gag ccc ccc agg aga tca gcc tgg acc ggt cac ggc<br>Asp Leu Pro Tyr Glu Pro Pro Arg Arg Ser Ala Trp Thr Gly His Gly<br>             235                   240                245 | 1013 |
| cac ccc acg ccc cag tcg aaa gct gct caa cca tct cct tcc aca gtg<br>His Pro Thr Pro Gln Ser Lys Ala Ala Gln Pro Ser Pro Ser Thr Val<br>         250                   255                  260 | 1061 |
| ccc aaa act gaa gac cag cgt cct cag tta gat cct tat cag att ctt<br>Pro Lys Thr Glu Asp Gln Arg Pro Gln Leu Asp Pro Tyr Gln Ile Leu<br>265                   270                     275 | 1109 |
| gga cca aca agt agc cgc ctt gca aat cca ggc agt ggc cag atc cag<br>Gly Pro Thr Ser Ser Arg Leu Ala Asn Pro Gly Ser Gly Gln Ile Gln<br>280                   285                  290                295 | 1157 |
| ctt tgg cag ttc ctc ctg gag ctc ctg tcg gac agc tcc aac tcc agc<br>Leu Trp Gln Phe Leu Leu Glu Leu Leu Ser Asp Ser Ser Asn Ser Ser<br>             300                   305                310 | 1205 |

-continued

| | |
|---|---|
| tgc atc acc tgg gaa ggc acc aac ggg gag ttc aag atg acg gat ccc<br>Cys Ile Thr Trp Glu Gly Thr Asn Gly Glu Phe Lys Met Thr Asp Pro<br>315                                 320                             325 | 1253 |
| gac gag gtg gcc cgg cgc tgg gga gag cgg aag agc aaa ccc aac atg<br>Asp Glu Val Ala Arg Arg Trp Gly Glu Arg Lys Ser Lys Pro Asn Met<br>330                                335                         340 | 1301 |
| aac tac gat aag ctc agc cgc gcc ctc cgt tac tat gac aag aac<br>Asn Tyr Asp Lys Leu Ser Arg Ala Leu Arg Tyr Tyr Asp Lys Asn<br>345                          350                        355 | 1349 |
| atc atg acc aag gtc cat ggg aag cgc tac gcc tac aag ttc gac ttc<br>Ile Met Thr Lys Val His Gly Lys Arg Tyr Ala Tyr Lys Phe Asp Phe<br>360                              365                        370                        375 | 1397 |
| cac ggg atc gcc cag gcc ctc cag ccc cac ccc ccg gag tca tct ctg<br>His Gly Ile Ala Gln Ala Leu Gln Pro His Pro Pro Glu Ser Ser Leu<br>                        380                              385                        390 | 1445 |
| tac aag tac ccc tca gac ctc ccg tac atg ggc tcc tat cac gcc cac<br>Tyr Lys Tyr Pro Ser Asp Leu Pro Tyr Met Gly Ser Tyr His Ala His<br>                   395                              400                        405 | 1493 |
| cca cag aag atg aac ttt gtg gcg ccc cac cct cca gcc ctc ccc gtg<br>Pro Gln Lys Met Asn Phe Val Ala Pro His Pro Pro Ala Leu Pro Val<br>        410                              415                            420 | 1541 |
| aca tct tcc agt ttt ttt gct gcc cca aac cca tac tgg aat tca cca<br>Thr Ser Ser Ser Phe Phe Ala Ala Pro Asn Pro Tyr Trp Asn Ser Pro<br>       425                              430                          435 | 1589 |
| act ggg ggt ata tac ccc aac act agg ctc ccc acc agc cat atg cct<br>Thr Gly Gly Ile Tyr Pro Asn Thr Arg Leu Pro Thr Ser His Met Pro<br>440                                445                         450                        455 | 1637 |
| tct cat ctg ggc act tac tac taa agacctggcg gaggcttttc ccatcagcgt<br>Ser His Leu Gly Thr Tyr Tyr<br>                   460 | 1691 |
| gcattcacca gcccatcgcc acaaactcta tcggagaaca tgaatcaaaa gtgcctcaag | 1751 |
| aggaatgaaa aaagctttac tggggctggg gaaggaagcc ggggaagaga tccaaagact | 1811 |
| cttgggaggg agttactgaa gtcttactac agaaatgagg aggatgctaa aaatgtcacg | 1871 |
| aatatggaca tatcatctgt ggactgacct tgtaaaagac agtgtatgta gaagcatgaa | 1931 |
| gtcttaagga caaagtgcca agaaagtgg tcttaagaaa tgtataaact ttagagtaga | 1991 |
| gtttggaatc ccactaatgc aaactgggat gaaactaaag caatagaaac aacacagttt | 2051 |
| tgacctaaca taccgtttat aatgccattt taaggaaaac tacctgtatt taaaaataga | 2111 |
| aacatatcaa aaacaagaga aaagacacga gagagactgt ggcccatcaa cagacgttga | 2171 |
| tatgcaactg catggcatgt gctgtttgg ttgaaatcaa atacattccg tttgatggac | 2231 |
| agctgtcagc tttctcaaac tgtgaagatg acccaaagtt tccaactcct ttacagtatt | 2291 |
| accgggacta tgaactaaaa ggtgggactg aggatgtgta tagagtgagc gtgtgattgt | 2351 |
| agacagaggg gtgaagaagg aggaggaaga ggcagagaag gaggagacca gggctgggaa | 2411 |
| agaaacttct caagcaatga agactggact caggacattt ggggactgtg tacaatgagt | 2471 |
| tatggagact cgagggttca tgcagtcagt gttataccaa acccagtgtt aggagaaagg | 2531 |
| acacagcgta atggagaaag gggaagtagt agaattcaga aacaaaaatg cgcatctctt | 2591 |
| tctttgtttg tcaaatgaaa attttaactg gaattgtctg atatttaaga gaaacattca | 2651 |
| ggacctcatc attatgtggg ggctttgttc tccacagggt caggtaagag atggccttct | 2711 |
| tggctgccac aatcagaaat cacgcaggca ttttgggtag gcggcctcca gttttccttt | 2771 |
| gagtcgcgaa cgctgtgcgt ttgtcagaat gaagtataca agtcaatgtt tttccccctt | 2831 |

```
tttatataat aattatataa cttatgcatt tatacactac gagttgatct cggccagcca    2891
aagacacacg acaaaagaga caatcgatat aatgtggcct tgaattttaa ctctgtatgc    2951
ttaatgttta caatatgaag ttattagttc ttagaatgca gaatgtatgt aataaaataa    3011
gcttggccta gcatggcaaa tcagatttat acaggagtct gcatttgcac ttttttagt    3071 gactaaagtt gcttaatgaa aacatgtgct gaatgttgtg gattttgtgt tataatttac    3131
tttgtccagg aacttgtgca agggagagcc aaggaaatag gatgtttggc acccaaatgg    3191
cgtcagcctc tccaggtcct tcttgcctcc cctcctgtct tttatttcta gccccttttg    3251
gaacagaagg accccgggtt tcacattgga gcctccatat ttatgcctgg aatggaaaga    3311
ggcctatgaa gctggggttg tcattgagaa attctagttc agcacctggt cacaaatcac    3371
ccttaattcc tgctatgatt aaaatacatt tgttgaacag tgaacaagct accactcgta    3431
aggcaaactg tattattact ggcaaataaa gcgtcatgga tagctgcaat ttctcacttt    3491
acagaaacaa gggataacgt ctagatttgc tgcggggttt ctctttcagg agctctcact    3551
aggtagacag ctttagtcct gctacatcag agttacctgg gcactgtggc ttgggattca    3611
ctagccctga gcctgatgtt gctggctatc ccttgaagac aatgtttatt tccataatct    3671
agagtcagtt tccctgggca tcttttcttt gaatcacaaa tgctgccaac cttggtccag    3731
gtgaaggcaa ctcaaaaggt gaaaatacaa ggtgaccgtg cgaaggcgct agccgaaaca    3791
tcttagctga ataggtttct gaactggccc ttttcatagc tgtttcaggg cctgtttttt    3851
tcacgttgca gtccttttgc tatgattatg tgaagttgcc aaacctctgt gctgtggatg    3911
ttttggcagt gggctttgaa gtcggcagga cacgattacc aatgctcctg acaccccgtg    3971
tcatttggat tagacggagc ccaaccatcc atcattttgc agcagcctgg gaaggcccac    4031
aaagtgcccg tatctcctta gggaaaataa ataaatacaa tcatgaaagc tggcagttag    4091
gctgacccaa actgtgctaa tggaaaagat cagtcatttt tattttggaa tgcaaagtca    4151
agacacacct acattcttca tagaaataca catttacttg gataatcact cagttctctc    4211
ttcaagactg tctcatgagc aagatcataa aaacaagaca tgattatcat attcaatttt    4271
aacagatgtt ttccattaga tccctcaacc ctccaccccc agtccaggtt attagcaagt    4331
cttatgagca actgggataa ttttggataa catgataata ctgagttcct tcaaatacat    4391
aattcttaaa ttgtttcaaa atggcattaa ctctctgtta ctgttgtaat ctaattccaa    4451 agcccctcc aggtcatatt cataattgca tgaacctttt ctctctgttt gtccctgtct    4511
cttggcttgc cctgatgtat actcagactc ctgtacaatc ttactcctgc tggcaagaga    4571
tttgtcttct tttcttgtct tcaattggct ttcgggcctt gtatgtggta aaatcaccaa    4631
atcacagtca agactgtgtt tttgttccta gtttgatgcc cttatgtccc ggaggggttc    4691
acaaagtgct ttgtcaggac tgctgcagtt agaaggctca ctgcttctcc taagccttct    4751
gcacagatgt ggcacctgca acccaggagc aggagccgga ggagctgccc tctgacagca    4811
ggtgcagcag agatggctac agctcaggag ctggaaggt gatggggcac agggaaagca    4871
cagatgttct gcagcgcccc aaagtgaccc attgcctgga gaaagagaag aaaatatttt    4931
ttaaaaagct agtttattta gcttctcatt aattcattca aataaagtcg tgaggtgact    4991
aattagagaa taaaaattac tttggactac tcaaaaatac accaaaaaaa a             5042
```

<210> SEQ ID NO 3
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 3
gcgcgcctcg gccaggaagc cttatcagtt                                30

<210> SEQ ID NO 4
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 4
gagtttgatg tccaggaagc cttatcagtt                                30

<210> SEQ ID NO 5
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 5
gtggagaaag gggaggaagc cttatcagtt                                30

<210> SEQ ID NO 6
<211> LENGTH: 3183
<212> TYPE: DNA
<213> ORGANISM: Homo sapiens

<400> SEQUENCE: 6
aacaaacctc gcctggctcc cagctggtgc tgaagctcgt cagttcacca tccgccctcg    60
gcttccgcgg ggcgctgggc cgccagcctc ggcaccgtcc tttcctttct ccctcgcgtt   120
aggcaggtga cagcagggac atgtctcggg agatgcagga tgtagacctc gctgaggtga   180
agccttttgg ggagaaaggg agaccatca ccggcctcct gcaagagttt gatgtccagg    240
aagccttatc agttgtgagt gaggaccagt cgttgtttga gtgtgcctac ggaacgccac   300
acctggctaa gacagagatg accgcgtcct cctccagcga ctatggacag acttccaaga   360
tgagcccacg cgtccctcag caggattggc tgtctcaacc cccagccagg gtcaccatca   420
aaatggaatg taaccctagc caggtgaatg ctcaaggaa ctctcctgat gaatgcagtg    480
tggccaaagg cgggaagatg gtgggcagcc agacaccgt tgggatgaac tacggcagct   540
acatggagga gaagcacatg ccacccccaa acatgaccac gaacgagcgc agagttatcg   600
tgccagcaga tcctacgcta tggagtacag accatgtgcg gcagtggctg agtgggcgg    660
tgaaagaata tggccttcca gacgtcaaca tcttgttatt ccagaacatc gatgggaagg   720
aactgtgcaa gatgaccaag gacgacttcc agaggctcac ccccagctac aacgccgaca   780
tccttctctc acatctccac tacctcagag agactcctct tccacatttg acttcagatg   840
atgttgataa agccttacaa aactctccac ggttaatgca tgctagaaac acaggggtg    900
cagcttttat tttcccaaat acttcagtat atcctgaagc tacgcaaaga attacaacta   960
ggccagattt accatatgag cccccccagga gatcagcctg gaccggtcac ggccacccca  1020
cgccccagtc gaaagctgct caaccatctc cttccacagt gcccaaaact gaagaccagc   1080
gtcctcagtt agatccttat cagattcttg gaccaacaag tagccgcctt gcaaatccag   1140
gcagtggcca gatccagctt tggcagttcc tcctggagct cctgtcggac agctccaact   1200

```
ccagctgcat cacctgggaa ggcaccaacg gggagttcaa gatgacggat cccgacgagg    1260
tggcccggcg ctggggagag cggaagagca aacccaacat gaactacgat aagctcagcc    1320
gcgccctccg ttactactat gacaagaaca tcatgaccaa ggtccatggg aagcgctacg    1380
cctacaagtt cgacttccac gggatcgccc aggccctcca gccccacccc cggagtcat     1440 ctctgtacaa gtaccoctca gacctcccgt acatgggctc ctatcacgcc cacccacaga    1500
agatgaactt tgtggcgccc caccctccag ccctccccgt gacatcttcc agttttttg     1560 ctgccccaaa cccatactgg aattcaccaa ctggggtat ataccccaac actaggctcc      1620
ccaccagcca tatgccttct catctgggca cttactacta aagacctggc ggaggctttt    1680
cccatcagcg tgcattcacc agcccatcgc cacaaactct atcggagaac atgaatcaaa    1740
agtgcctcaa gaggaatgaa aaaagcttta ctggggctgg ggaaggaagc cggggaagag    1800
atccaaagac tcttgggagg gagttactga agtcttacta cagaaatgag gaggatgcta    1860
aaaatgtcac gaatatggac atatcatctg tggactgacc ttgtaaaaga cagtgtatgt    1920
agaagcatga agtcttaagg acaaagtgcc aaagaaagtg gtcttaagaa atgtataaac    1980
tttagagtag agtttggaat cccactaatg caaactggga tgaaactaaa gcaatagaaa    2040
caacacagtt ttgacctaac ataccgttta taatgccatt ttaaggaaaa ctacctgtat    2100
ttaaaaatag aaacatatca aaaacaagag aaaagacacg agagagactg tggcccatca    2160
acagacgttg atatgcaact gcatggcatg tgctgttttg gttgaaatca aatacattcc    2220
gtttgatgga cagctgtcag ctttctcaaa ctgtgaagat gacccaaagt ttccaactcc    2280
tttacagtat taccgggact atgaactaaa aggtgggact gaggatgtgt atagagtgag    2340
cgtgtgattg tagacagagg ggtgaagaag gaggaggaag aggcagagaa ggaggagacc    2400
aggctgggaa agaaacttct caagcaatga agactggact caggacattt ggggactgtg    2460
tacaatgagt tatggagact cgagggttca tgcagtcagt gttataccaa acccagtgtt    2520
aggagaaagg acacagcgta atggagaaag ggaagtagta gaattcagaa acaaaaatgc    2580
gcatctcttt ctttgtttgt caaatgaaaa ttttaactgg aattgtctga tatttaagag    2640
aaacattcag gacctcatca ttatgtgggg gcttttgttct ccacagggtc aggtaagaga    2700
tggccttctt ggctgccaca atcagaaatc acgcaggcat tttgggtagg cggcctccag    2760
ttttcctttg agtcgcgaac gctgtgcgtt tgtcagaatg aagtatacaa gtcaatgttt    2820 ttccccccttt ttatataata attatataac ttatgcattt atacactacg agttgatctc    2880
ggccagccaa agacacacga caaaagagac aatcgatata atgtggcctt gaatttttaac   2940 tctgtatgct taatgtttac aatatgaagt tattagttct tagaatgcag aatgtatgta    3000
ataaaataag cttggcctag catggcaaat cagatttata caggagtctg catttgcact    3060 tttttttagtg actaaagttg cttaatgaaa acatgtgctg aatgttgtgg atttttgtgtt  3120 ataatttact ttgtccagga acttgtgcaa gggagagcca aggaaatagg atgtttggca    3180
ccc                                                                  3183

<210> SEQ ID NO 7
<211> LENGTH: 506
<212> TYPE: PRT
<213> ORGANISM: Homo sapiens

<400> SEQUENCE: 7

Met Ser Arg Glu Met Gln Asp Val Asp Leu Ala Glu Val Lys Pro Leu
1               5                   10                  15
```

-continued

Val Glu Lys Gly Glu Thr Ile Thr Gly Leu Leu Gln Glu Phe Asp Val
         20                  25                  30

Gln Glu Ala Leu Ser Val Ser Glu Asp Gln Ser Leu Phe Glu Cys
         35                  40                  45

Ala Tyr Gly Thr Pro His Leu Ala Lys Thr Glu Met Thr Ala Ser Ser
 50                  55                  60

Ser Ser Asp Tyr Gly Gln Thr Ser Lys Met Ser Pro Arg Val Pro Gln
65                  70                  75                  80

Gln Asp Trp Leu Ser Gln Pro Pro Ala Arg Val Thr Ile Lys Met Glu
                 85                  90                  95

Cys Asn Pro Ser Gln Val Asn Gly Ser Arg Asn Ser Pro Asp Glu Cys
             100                 105                 110

Ser Val Ala Lys Gly Gly Lys Met Val Gly Ser Pro Asp Thr Val Gly
         115                 120                 125

Met Asn Tyr Gly Ser Tyr Met Glu Glu Lys His Met Pro Pro Pro Asn
     130                 135                 140

Met Thr Thr Asn Glu Arg Arg Val Ile Val Pro Ala Asp Pro Thr Leu
145                 150                 155                 160

Trp Ser Thr Asp His Val Arg Gln Trp Leu Glu Trp Ala Val Lys Glu
                 165                 170                 175

Tyr Gly Leu Pro Asp Val Asn Ile Leu Leu Phe Gln Asn Ile Asp Gly
             180                 185                 190

Lys Glu Leu Cys Lys Met Thr Lys Asp Asp Phe Gln Arg Leu Thr Pro
         195                 200                 205

Ser Tyr Asn Ala Asp Ile Leu Leu Ser His Leu His Tyr Leu Arg Glu
     210                 215                 220

Thr Pro Leu Pro His Leu Thr Ser Asp Val Asp Lys Ala Leu Gln
225                 230                 235                 240

Asn Ser Pro Arg Leu Met His Ala Arg Asn Thr Gly Gly Ala Ala Phe
                 245                 250                 255

Ile Phe Pro Asn Thr Ser Val Tyr Pro Glu Ala Thr Gln Arg Ile Thr
             260                 265                 270

Thr Arg Pro Asp Leu Pro Tyr Glu Pro Pro Arg Arg Ser Ala Trp Thr
         275                 280                 285

Gly His Gly His Pro Thr Pro Gln Ser Lys Ala Ala Gln Pro Ser Pro
     290                 295                 300

Ser Thr Val Pro Lys Thr Glu Asp Gln Arg Pro Gln Leu Asp Pro Tyr
305                 310                 315                 320

Gln Ile Leu Gly Pro Thr Ser Ser Arg Leu Ala Asn Pro Gly Ser Gly
                 325                 330                 335

Gln Ile Gln Leu Trp Gln Phe Leu Leu Glu Leu Leu Ser Asp Ser Ser
             340                 345                 350

Asn Ser Ser Cys Ile Thr Trp Glu Gly Thr Asn Gly Glu Phe Lys Met
         355                 360                 365

Thr Asp Pro Asp Glu Val Ala Arg Arg Trp Gly Glu Arg Lys Ser Lys
     370                 375                 380

Pro Asn Met Asn Tyr Asp Lys Leu Ser Arg Ala Leu Arg Tyr Tyr Tyr
385                 390                 395                 400

Asp Lys Asn Ile Met Thr Lys Val His Gly Lys Arg Tyr Ala Tyr Lys
                 405                 410                 415

Phe Asp Phe His Gly Ile Ala Gln Ala Leu Gln Pro His Pro Pro Glu
             420                 425                 430

Ser Ser Leu Tyr Lys Tyr Pro Ser Asp Leu Pro Tyr Met Gly Ser Tyr

His Ala His Pro Gln Lys Met Asn Phe Val Ala Pro His Pro Pro Ala
    450                 455                 460

Leu Pro Val Thr Ser Ser Phe Phe Ala Ala Pro Asn Pro Tyr Trp
465                 470                 475                 480

Asn Ser Pro Thr Gly Gly Ile Tyr Pro Asn Thr Arg Leu Pro Thr Ser
                485                 490                 495

His Met Pro Ser His Leu Gly Thr Tyr Tyr
            500                 505

<210> SEQ ID NO 8
<211> LENGTH: 3147
<212> TYPE: DNA
<213> ORGANISM: Homo sapiens

<400> SEQUENCE: 8

| | | | | | |
|---|---|---|---|---|---|
| aacaaacctc | gcctggctcc | cagctggtgc | tgaagctcgt | cagttcacca | tccgccctcg | 60 |
| gcttccgcgg | ggcgctgggc | cgccagcctc | ggcaccgtcc | tttcctttct | ccctcgcgtt | 120 |
| aggcaggtga | cagcagggac | atgtctcggg | agatgcagga | tgtagacctc | gctgaggtga | 180 |
| agcctttggt | ggagaaaggg | gaggaagcct | tatcagttgt | gagtgaggac | cagtcgttgt | 240 |
| ttgagtgtgc | ctacggaacg | ccacacctgg | ctaagacaga | gatgaccgcg | tcctcctcca | 300 |
| gcgactatgg | acagacttcc | aagatgagcc | acgcgtcccc | tcagcaggat | ggctgtctc | 360 |
| aaccccccagc | cagggtcacc | atcaaaatgg | aatgtaaccc | tagccaggtg | aatggctcaa | 420 |
| ggaactctcc | tgatgaatgc | agtgtggcca | aggcgggaa | gatggtgggc | agcccagaca | 480 |
| ccgttgggat | gaactacggc | agctacatgg | aggagaagca | catgccaccc | ccaaacatga | 540 |
| ccacgaacga | gcgcagagtt | atcgtgccag | cagatcctac | gctatggagt | acagaccatg | 600 |
| tgcggcagtg | gctggagtgg | gcggtgaaag | aatatggcct | tccagacgtc | aacatcttgt | 660 |
| tattccagaa | catcgatggg | aaggaactgt | gcaagatgac | caaggacgac | ttccagaggc | 720 |
| tcacccccag | ctacaacgcc | gacatccttc | tctcacatct | ccactacctc | agagagactc | 780 |
| ctcttccaca | tttgacttca | gatgatgttg | ataaagcctt | acaaaactct | ccacggttaa | 840 |
| tgcatgctag | aaacacaggg | ggtgcagctt | ttattttccc | aaatacttca | gtatatcctg | 900 |
| aagctacgca | aagaattaca | actaggccag | atttaccata | tgagccccc | aggagatcag | 960 |
| cctggaccgg | tcacggccac | cccacgcccc | agtcgaaagc | tgctcaacca | tctccttcca | 1020 |
| cagtgcccaa | aactgaagac | cagcgtcctc | agttagatcc | ttatcagatt | cttggaccaa | 1080 |
| caagtagccg | ccttgcaaat | ccaggcagtg | gccagatcca | gctttggcag | ttcctcctgg | 1140 |
| agctcctgtc | ggacagctcc | aactccagct | gcatcacctg | ggaaggcacc | aacggggagt | 1200 |
| tcaagatgac | ggatcccgac | gaggtggccc | ggcgctgggg | agagcggaag | agcaaaccca | 1260 |
| acatgaacta | cgataagctc | agccgcgccc | tccgttacta | ctatgacaag | aacatcatga | 1320 |
| ccaaggtcca | tgggaagcgc | tacgcctaca | agttcgactt | ccacgggatc | gcccaggccc | 1380 |
| tccagcccca | ccccggag | tcatctctgt | acaagtaccc | ctcagacctc | cgtacatgg | 1440 |
| gctcctatca | cgcccaccca | cagaagatga | actttgtggc | ccccaccct | ccagccctcc | 1500 |
| ccgtgacatc | ttccagtttt | tttgctgccc | caaacccata | ctggaattca | ccaactgggg | 1560 |
| gtatataccc | caacactagg | ctccccacca | gccatgcc | ttctcatctg | ggcacttact | 1620 |
| actaaagacc | tggcggaggc | ttttcccatc | agcgtgcatt | caccagccca | tcgccacaaa | 1680 |
| ctctatcgga | gaacatgaat | caaaagtgcc | tcaagaggaa | tgaaaaaagc | tttactgggg | 1740 |

```
ctggggaagg aagccgggga agagatccaa agactcttgg gagggagtta ctgaagtctt    1800
actacagaaa tgaggaggat gctaaaaatg tcacgaatat ggacatatca tctgtggact    1860
gaccttgtaa aagacagtgt atgtagaagc atgaagtctt aaggacaaag tgccaaagaa    1920
agtggtctta agaaatgtat aaactttaga gtagagtttg gaatcccact aatgcaaact    1980
gggatgaaac taaagcaata gaaacaacac agttttgacc taacataccg tttataatgc    2040
cattttaagg aaaactacct gtatttaaaa atagaaacat atcaaaaaca agagaaaaga    2100
cacgagagag actgtggccc atcaacagac gttgatatgc aactgcatgg catgtgctgt    2160
tttggttgaa atcaaataca ttccgtttga tggacagctg tcagctttct caaactgtga    2220
agatgaccca agtttccaa ctcctttaca gtattaccgg gactatgaac taaaaggtgg    2280
gactgaggat gtgtatagag tgagcgtgtg attgtagaca gaggggtgaa gaaggaggag    2340
gaagaggcag agaaggagga gaccaggctg ggaaagaaac ttctcaagca atgaagactg    2400
gactcaggac atttggggac tgtgtacaat gagttatgga gactcgaggg ttcatgcagt    2460
cagtgttata ccaaacccag tgttaggaga aaggacacag cgtaatggag aaagggaagt    2520
agtagaattc agaaacaaaa atgcgcatct cttttcttgt ttgtcaaatg aaaattttaa    2580
ctggaattgt ctgatattta agagaaacat tcaggacctc atcattatgt gggggctttg    2640
ttctccacag ggtcaggtaa gagatggcct tcttggctgc acaatcaga aatcacgcag     2700 gcattttggg taggcggcct ccagttttcc tttgagtcgc gaacgctgtg cgtttgtcag    2760
aatgaagtat acaagtcaat gttttccccc cttttatat aataattata taacttatgc     2820
atttatacac tacgagttga tctcggccag ccaaagacac acgacaaaag agacaatcga    2880
tataatgtgg ccttgaattt taactctgta tgcttaatgt ttacaatatg aagttattag    2940
ttcttagaat gcagaatgta tgtaataaaa taagcttggc ctagcatggc aaatcagatt    3000
tatacaggag tctgcatttg cacttttttt agtgactaaa gttgcttaat gaaaacatgt    3060
gctgaatgtt gtggattttg tgttataatt tactttgtcc aggaacttgt gcaagggaga    3120
gccaaggaaa taggatgttt ggcaccc                                        3147
```

<210> SEQ ID NO 9
<211> LENGTH: 494
<212> TYPE: PRT
<213> ORGANISM: Homo sapiens

<400> SEQUENCE: 9

```
Met Ser Arg Glu Met Gln Asp Val Asp Leu Ala Glu Val Lys Pro Leu
1               5                   10                  15

Val Glu Lys Gly Glu Glu Ala Leu Ser Val Val Ser Glu Asp Gln Ser
            20                  25                  30

Leu Phe Glu Cys Ala Tyr Gly Thr Pro His Leu Ala Lys Thr Glu Met
        35                  40                  45

Thr Ala Ser Ser Ser Asp Tyr Gly Gln Thr Ser Lys Met Ser Pro
    50                  55                  60

Arg Val Pro Gln Gln Asp Trp Leu Ser Gln Pro Pro Ala Arg Val Thr
65                  70                  75                  80

Ile Lys Met Glu Cys Asn Pro Ser Gln Val Asn Gly Ser Arg Asn Ser
                85                  90                  95

Pro Asp Glu Cys Ser Val Ala Lys Gly Gly Lys Met Val Gly Ser Pro
            100                 105                 110

Asp Thr Val Gly Met Asn Tyr Gly Ser Tyr Met Glu Glu Lys His Met
```

```
            115                 120                 125
Pro Pro Pro Asn Met Thr Thr Asn Glu Arg Arg Val Ile Val Pro Ala
    130                 135                 140

Asp Pro Thr Leu Trp Ser Thr Asp His Val Arg Gln Trp Leu Glu Trp
145                 150                 155                 160

Ala Val Lys Glu Tyr Gly Leu Pro Asp Val Asn Ile Leu Leu Phe Gln
                165                 170                 175

Asn Ile Asp Gly Lys Glu Leu Cys Lys Met Thr Lys Asp Asp Phe Gln
            180                 185                 190

Arg Leu Thr Pro Ser Tyr Asn Ala Asp Ile Leu Leu Ser His Leu His
        195                 200                 205

Tyr Leu Arg Glu Thr Pro Leu Pro His Leu Thr Ser Asp Asp Val Asp
210                 215                 220

Lys Ala Leu Gln Asn Ser Pro Arg Leu Met His Ala Arg Asn Thr Gly
225                 230                 235                 240

Gly Ala Ala Phe Ile Phe Pro Asn Thr Ser Val Tyr Pro Glu Ala Thr
                245                 250                 255

Gln Arg Ile Thr Thr Arg Pro Asp Leu Pro Tyr Glu Pro Pro Arg Arg
            260                 265                 270

Ser Ala Trp Thr Gly His Gly His Pro Thr Pro Gln Ser Lys Ala Ala
        275                 280                 285

Gln Pro Ser Pro Ser Thr Val Pro Lys Thr Glu Asp Gln Arg Pro Gln
290                 295                 300

Leu Asp Pro Tyr Gln Ile Leu Gly Pro Thr Ser Ser Arg Leu Ala Asn
305                 310                 315                 320

Pro Gly Ser Gly Gln Ile Gln Leu Trp Gln Phe Leu Leu Glu Leu Leu
                325                 330                 335

Ser Asp Ser Ser Asn Ser Ser Cys Ile Thr Trp Glu Gly Thr Asn Gly
            340                 345                 350

Glu Phe Lys Met Thr Asp Pro Asp Glu Val Ala Arg Arg Trp Gly Glu
        355                 360                 365

Arg Lys Ser Lys Pro Asn Met Asn Tyr Asp Lys Leu Ser Arg Ala Leu
370                 375                 380

Arg Tyr Tyr Tyr Asp Lys Asn Ile Met Thr Lys Val His Gly Lys Arg
385                 390                 395                 400

Tyr Ala Tyr Lys Phe Asp Phe His Gly Ile Ala Gln Ala Leu Gln Pro
                405                 410                 415

His Pro Pro Glu Ser Ser Leu Tyr Lys Tyr Pro Ser Asp Leu Pro Tyr
            420                 425                 430

Met Gly Ser Tyr His Ala His Pro Gln Lys Met Asn Phe Val Ala Pro
        435                 440                 445

His Pro Pro Ala Leu Pro Val Thr Ser Ser Phe Phe Ala Ala Pro
450                 455                 460

Asn Pro Tyr Trp Asn Ser Pro Thr Gly Gly Ile Tyr Pro Asn Thr Arg
465                 470                 475                 480

Leu Pro Thr Ser His Met Pro Ser His Leu Gly Thr Tyr Tyr
                485                 490

<210> SEQ ID NO 10
<211> LENGTH: 21
<212> TYPE: DNA
<213> ORGANISM: Artificial Sequence
<220> FEATURE:
<223> OTHER INFORMATION: Synthetic oligonucleotide primer
```

<400> SEQUENCE: 10
taggcgcgag ctaagcagga g                                      21

<210> SEQ ID NO 11
<211> LENGTH: 25
<212> TYPE: DNA
<213> ORGANISM: Artificial Sequence
<220> FEATURE:
<223> OTHER INFORMATION: Synthetic oligonucleotide primer

<400> SEQUENCE: 11
gtaggcacac tcaaacaacg actgg                                  25

<210> SEQ ID NO 12
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 12
taggcgcgag ctaagcagga g                                      21

<210> SEQ ID NO 13
<211> LENGTH: 24
<212> TYPE: DNA
<213> ORGANISM: Artificial Sequence
<220> FEATURE:
<223> OTHER INFORMATION: Synthetic oligonucleotide primer

<400> SEQUENCE: 13
ccatattctt tcaccgccca ctcc                                   24

<210> SEQ ID NO 14
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 14
taggcgcgag ctaagcagga g                                      21

<210> SEQ ID NO 15
<211> LENGTH: 18
<212> TYPE: DNA
<213> ORGANISM: Artificial Sequence
<220> FEATURE:
<223> OTHER INFORMATION: Synthetic oligonucleotide primer

<400> SEQUENCE: 15
cgactggggc gtggggtg                                          18

<210> SEQ ID NO 16
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 16
taggcgcgag ctaagcagga g                                      21

<210> SEQ ID NO 17
<211> LENGTH: 27

```
<212> TYPE: DNA
<213> ORGANISM: Artificial Sequence
<220> FEATURE:
<223> OTHER INFORMATION: Synthetic oligonucleotide primer

<400> SEQUENCE: 17
ttagtagtaa gtgcccagat gagaagg                                          27

<210> SEQ ID NO 18
<211> LENGTH: 24
<212> TYPE: DNA
<213> ORGANISM: Artificial Sequence
<220> FEATURE:
<223> OTHER INFORMATION: Synthetic oligonucleotide primer

<400> SEQUENCE: 18
cgcagagtta tcgtgccagc agat                                             24

<210> SEQ ID NO 19
<211> LENGTH: 24
<212> TYPE: DNA
<213> ORGANISM: Artificial Sequence
<220> FEATURE:
<223> OTHER INFORMATION: Synthetic oligonucleotide primer

<400> SEQUENCE: 19
ccatattctt tcaccgccca ctcc                                             24

<210> SEQ ID NO 20
<211> LENGTH: 24
<212> TYPE: DNA
<213> ORGANISM: Artificial Sequence
<220> FEATURE:
<223> OTHER INFORMATION: Synthetic oligonucleotide primer

<400> SEQUENCE: 20
gcccgccaga agatgagtga aatc                                             24

<210> SEQ ID NO 21
<211> LENGTH: 24
<212> TYPE: DNA
<213> ORGANISM: Artificial Sequence
<220> FEATURE:
<223> OTHER INFORMATION: Synthetic oligonucleotide primer

<400> SEQUENCE: 21
accaacagac gagagagccc tttc                                             24

<210> SEQ ID NO 22
<211> LENGTH: 24
<212> TYPE: DNA
<213> ORGANISM: Artificial Sequence
<220> FEATURE:
<223> OTHER INFORMATION: Synthetic oligonucleotide primer

<400> SEQUENCE: 22
attgactcct catgctggga ctgg                                             24

<210> SEQ ID NO 23
<211> LENGTH: 22
<212> TYPE: DNA
<213> ORGANISM: Artificial Sequence
<220> FEATURE:
<223> OTHER INFORMATION: Synthetic oligonucleotide primer

<400> SEQUENCE: 23
```
cggtataggg ctggacgatg gg                                              22

<210> SEQ ID NO 24
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 24
taggcgcgag ctaagcagga g                                               21

<210> SEQ ID NO 25
<211> LENGTH: 25
<212> TYPE: DNA
<213> ORGANISM: Artificial Sequence
<220> FEATURE:
<223> OTHER INFORMATION: Synthetic oligonucleotide primer

<400> SEQUENCE: 25
gtaggcacac tcaaacaacg actgg                                           25

<210> SEQ ID NO 26
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 26
ccatcatcct ggcaacagct                                                 20

<210> SEQ ID NO 27
<211> LENGTH: 19
<212> TYPE: DNA
<213> ORGANISM: Artificial Sequence
<220> FEATURE:
<223> OTHER INFORMATION: Synthetic oligonucleotide primer

<400> SEQUENCE: 27
gcattcctca gggtgcagg                                                  19

<210> SEQ ID NO 28
<211> LENGTH: 18
<212> TYPE: DNA
<213> ORGANISM: Artificial Sequence
<220> FEATURE:
<223> OTHER INFORMATION: Synthetic oligonucleotide primer

<400> SEQUENCE: 28
cgctggctcc gggtgaca                                                   18

<210> SEQ ID NO 29
<211> LENGTH: 24
<212> TYPE: DNA
<213> ORGANISM: Artificial Sequence
<220> FEATURE:
<223> OTHER INFORMATION: Synthetic oligonucleotide primer

<400> SEQUENCE: 29
ccatattctt tcaccgccca ctcc                                            24

<210> SEQ ID NO 30
<211> LENGTH: 18
<212> TYPE: DNA
<213> ORGANISM: Artificial Sequence

```
<220> FEATURE:
<223> OTHER INFORMATION: Synthetic oligonucleotide primer

<400> SEQUENCE: 30
cgactggggc gtggggtg                                                  18

<210> SEQ ID NO 31
<211> LENGTH: 23
<212> TYPE: DNA
<213> ORGANISM: Artificial Sequence
<220> FEATURE:
<223> OTHER INFORMATION: Synthetic oligonucleotide primer

<400> SEQUENCE: 31
gtcccaagta cgtccacggt cag                                            23

<210> SEQ ID NO 32
<211> LENGTH: 24
<212> TYPE: DNA
<213> ORGANISM: Artificial Sequence
<220> FEATURE:
<223> OTHER INFORMATION: Synthetic oligonucleotide primer

<400> SEQUENCE: 32
ccatattctt tcaccgccca ctcc                                           24

<210> SEQ ID NO 33
<211> LENGTH: 18
<212> TYPE: DNA
<213> ORGANISM: Artificial Sequence
<220> FEATURE:
<223> OTHER INFORMATION: Synthetic oligonucleotide primer

<400> SEQUENCE: 33
cgactggggc gtggggtg                                                  18

<210> SEQ ID NO 34
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 34
tgcgggaaat cgggctgaag                                                20

<210> SEQ ID NO 35
<211> LENGTH: 24
<212> TYPE: DNA
<213> ORGANISM: Artificial Sequence
<220> FEATURE:
<223> OTHER INFORMATION: Synthetic oligonucleotide primer

<400> SEQUENCE: 35
ccatattctt tcaccgccca ctcc                                           24

<210> SEQ ID NO 36
<211> LENGTH: 18
<212> TYPE: DNA
<213> ORGANISM: Artificial Sequence
<220> FEATURE:
<223> OTHER INFORMATION: Synthetic oligonucleotide primer

<400> SEQUENCE: 36
cgactggggc gtggggtg                                                  18
```

<210> SEQ ID NO 37
<211> LENGTH: 24
<212> TYPE: DNA
<213> ORGANISM: Artificial Sequence
<220> FEATURE:
<223> OTHER INFORMATION: Synthetic oligonucleotide primer

<400> SEQUENCE: 37
caactaacac tgcggcttcc tgag                                          24

<210> SEQ ID NO 38
<211> LENGTH: 24
<212> TYPE: DNA
<213> ORGANISM: Artificial Sequence
<220> FEATURE:
<223> OTHER INFORMATION: Synthetic oligonucleotide primer

<400> SEQUENCE: 38
ccatattctt tcaccgccca ctcc                                          24

<210> SEQ ID NO 39
<211> LENGTH: 18
<212> TYPE: DNA
<213> ORGANISM: Artificial Sequence
<220> FEATURE:
<223> OTHER INFORMATION: Synthetic oligonucleotide primer

<400> SEQUENCE: 39
cgactggggc gtggggtg                                                 18

<210> SEQ ID NO 40
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 40
gctggagaaa caaaccctct                                               20

<210> SEQ ID NO 41
<211> LENGTH: 24
<212> TYPE: DNA
<213> ORGANISM: Artificial Sequence
<220> FEATURE:
<223> OTHER INFORMATION: Synthetic oligonucleotide primer

<400> SEQUENCE: 41
ccatattctt tcaccgccca ctcc                                          24

<210> SEQ ID NO 42
<211> LENGTH: 18
<212> TYPE: DNA
<213> ORGANISM: Artificial Sequence
<220> FEATURE:
<223> OTHER INFORMATION: Synthetic oligonucleotide primer

<400> SEQUENCE: 42
cgactggggc gtggggtg                                                 18

<210> SEQ ID NO 43
<211> LENGTH: 18
<212> TYPE: DNA
<213> ORGANISM: Artificial Sequence
<220> FEATURE:
<223> OTHER INFORMATION: Synthetic oligonucleotide primer

```
<400> SEQUENCE: 43
agccaagccc cgccgatc                                                 18

<210> SEQ ID NO 44
<211> LENGTH: 24
<212> TYPE: DNA
<213> ORGANISM: Artificial Sequence
<220> FEATURE:
<223> OTHER INFORMATION: Synthetic oligonucleotide primer

<400> SEQUENCE: 44
ccatattctt tcaccgccca ctcc                                           24

<210> SEQ ID NO 45
<211> LENGTH: 18
<212> TYPE: DNA
<213> ORGANISM: Artificial Sequence
<220> FEATURE:
<223> OTHER INFORMATION: Synthetic oligonucleotide primer

<400> SEQUENCE: 45
cgactggggc gtggggtg                                                 18

<210> SEQ ID NO 46
<211> LENGTH: 22
<212> TYPE: DNA
<213> ORGANISM: Artificial Sequence
<220> FEATURE:
<223> OTHER INFORMATION: Synthetic oligonucleotide primer

<400> SEQUENCE: 46
tctctccatc gccttgtctg tg                                            22

<210> SEQ ID NO 47
<211> LENGTH: 24
<212> TYPE: DNA
<213> ORGANISM: Artificial Sequence
<220> FEATURE:
<223> OTHER INFORMATION: Synthetic oligonucleotide primer

<400> SEQUENCE: 47
ccatattctt tcaccgccca ctcc                                           24

<210> SEQ ID NO 48
<211> LENGTH: 18
<212> TYPE: DNA
<213> ORGANISM: Artificial Sequence
<220> FEATURE:
<223> OTHER INFORMATION: Synthetic oligonucleotide primer

<400> SEQUENCE: 48
cgactggggc gtggggtg                                                 18

<210> SEQ ID NO 49
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 49
agaggtcaca actgcccgaa g                                             21

<210> SEQ ID NO 50
```

```
<211> LENGTH: 24
<212> TYPE: DNA
<213> ORGANISM: Artificial Sequence
<220> FEATURE:
<223> OTHER INFORMATION: Synthetic oligonucleotide primer

<400> SEQUENCE: 50
ccatattctt tcaccgccca ctcc                                          24

<210> SEQ ID NO 51
<211> LENGTH: 18
<212> TYPE: DNA
<213> ORGANISM: Artificial Sequence
<220> FEATURE:
<223> OTHER INFORMATION: Synthetic oligonucleotide primer

<400> SEQUENCE: 51
cgactggggc gtggggtg                                                 18

<210> SEQ ID NO 52
<211> LENGTH: 24
<212> TYPE: DNA
<213> ORGANISM: Artificial Sequence
<220> FEATURE:
<223> OTHER INFORMATION: Synthetic oligonucleotide primer

<400> SEQUENCE: 52
ctgaagctcg tcagttcacc atcc                                          24

<210> SEQ ID NO 53
<211> LENGTH: 24
<212> TYPE: DNA
<213> ORGANISM: Artificial Sequence
<220> FEATURE:
<223> OTHER INFORMATION: Synthetic oligonucleotide primer

<400> SEQUENCE: 53
ccatattctt tcaccgccca ctcc                                          24

<210> SEQ ID NO 54
<211> LENGTH: 18
<212> TYPE: DNA
<213> ORGANISM: Artificial Sequence
<220> FEATURE:
<223> OTHER INFORMATION: Synthetic oligonucleotide primer

<400> SEQUENCE: 54
cgactggggc gtggggtg                                                 18

<210> SEQ ID NO 55
<211> LENGTH: 27
<212> TYPE: DNA
<213> ORGANISM: Artificial Sequence
<220> FEATURE:
<223> OTHER INFORMATION: Synthetic oligonucleotide primer

<400> SEQUENCE: 55
ttagtagtaa gtgcccagat gagaagg                                       27

<210> SEQ ID NO 56
<211> LENGTH: 24
<212> TYPE: DNA
<213> ORGANISM: Artificial Sequence
<220> FEATURE:
<223> OTHER INFORMATION: Synthetic oligonucleotide primer

<400> SEQUENCE: 56
```

-continued

```
<210> SEQ ID NO 57
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 57
cgttcgtggt catgtttggg                                                  20

<210> SEQ ID NO 58
<211> LENGTH: 23
<212> TYPE: DNA
<213> ORGANISM: Artificial Sequence
<220> FEATURE:
<223> OTHER INFORMATION: Synthetic oligonucleotide primer

<400> SEQUENCE: 58
gccacactgc attcatcagg aga                                              23
```

METHODS OF DIAGNOSING AND TREATING PROSTATE CANCER CHARACTERIZED BY NDRG1-ERG FUSION

CROSS-REFERENCE TO RELATED APPLICATION

This application claims the benefit of priority of U.S. Provisional Application No. 61/158,276, filed on Mar. 6, 2009.

GOVERNMENT FUNDING

This invention was made with Government support under Grant Number 50CA090381 and R01 CA125612-01 awarded by NIH's National Cancer Institute. The United States Government has certain rights in the invention.

FIELD OF THE INVENTION

This invention relates to cancer diagnosis and treatment. More specifically, the invention relates to compositions and methods for diagnosing and treating prostate cancer characterized by NDRG1-ERG fusion.

BACKGROUND OF THE INVENTION

The majority of prostate cancers detected through PSA screening harbor an acquired recurrent chromosomal rearrangement (Tomlins et al., *Science*, 310, 644-8, 2005). The promoter region of the androgen-regulated transmembrane protease, serine 2 (TMPRSS2) gene is most often fused to the coding region of members of the erythroblast transformation specific (ETS) family of transcription factors, most commonly v-ets erythroblastosis virus E26 oncogene homolog (avian) (ERG). The TMPRSS2-ERG fusion is observed in around 90% of tumors that over-express the oncogene ERG. Other, less common, fusion events occur involving ETS family members (ETV1, ETV4 and ETV5) fused to TMPRSS2 or other 5' partners that differ in their prostate specificity and response to androgen (SLC45A3, HERV-K, C15orf21, HNRPA2B1, FLJ35294, DDX5, CANT1 and KLK2, reviewed by Kumar-Sinha et al., *Nat Rev Cancer* 8(7):497-511, 2008; and more recently, ACSL3 (Attard et al., *Br J Cancer,* 99, 314-20, 2008)). Moreover, variations in the structure of the gene fusions in prostate cancer yielding different fusion transcript isoforms have been reported (Wang et al., *Cancer Res,* 66, 8347-51, 2006). ETS rearranged prostate cancer, similar to other translocation tumors, may represent a distinct molecular subclass of prostate cancer based on studies demonstrating characteristic morphologic features (Mosquera et al., *J Pathol* 212: 91-101 2007), natural history (Attard et al., *Oncogene* 27: 253-63, 2008; Demichelis et al., *Oncogene* 26: 4596-9, 2007) and specific genomic (Demichelis et al., *Genes Chromosomes Cancer* 48: 366-380, 2009) and expression profiles (Setlur et al., *J Natl Cancer Inst* 100: 815-25, 2008).

SUMMARY OF THE INVENTION

A novel gene fusion has been identified between NDRG1 (N-myc downstream regulated gene 1) and ERG (v-ets erythroblastosis virus E26 oncogene homolog) in prostate cancer over-expressing ERG. The NDRG1-ERG gene fusion is inducible by androgen and by estrogen, and encodes a fusion-specific protein. Compositions and methods useful for diagnosing and treating cancer including prostate cancer are provided herein.

In one aspect, the invention provides a method for diagnosing cancer such as prostate cancer based on detecting in a biological sample, the presence of an NDRG1-ERG fusion molecule. The biological sample can be any suitable sample obtained or derived from the patient, including for example, tissue, cells, blood, urine, semen, and prostatic secretions.

The NDRG1-ERG gene fusion can be detected at the genomic or chromosomal DNA, mRNA or protein level. Fusion nucleic acid molecules can be detected by using various nucleic acid-based techniques, including hybridization, amplification, and sequencing. Fusion proteins can be detected using a variety of assays known for detection of proteins, including, for example, SDS-gel analysis and immunoassays.

In some embodiments, the NDRG1-ERG fusion is detected at the chromosomal level using a fluorescent in situ hybridization assay (FISH). Either or both of a break apart FISH assay that detects translocation of the NDRG1 gene, and a fusion FISH assay that detects a genomic fusion between NDRG1 and ERG can be used.

In other embodiments, the NDRG1-ERG fusion is detected at the mRNA level by using a nucleic acid amplification method (e.g., RT-PCR), a nucleic acid hybridization method (Northern blot analysis), or a method that combines nucleic acid amplification and nucleic acid hybridization.

For detection of an NDRG1-ERG fusion mRNA in an amplification method, one can utilizes a first primer specific for a 5' region of an NDRG1 mRNA, and a second primer specific for a 3' region of an ERG mRNA.

Detection of an NDRG1-ERG fusion mRNA can also be achieved in an amplification or hybridization method by using an oligonucleotide primer or probe specific for the junction of the fusion mRNA. Junctions of two fusion transcript variants are shown in FIG. 4A and FIG. 5A, and more locally in FIG. 2B.

In still other embodiments, the NDRG1-ERG fusion is detected at the protein level. For example, detection can be directed to an NDRG1-ERG fusion protein containing the amino acid sequence as set forth in SEQ ID NO: 7 or 9. Such fusion protein can be detected in an immunoassay using an antibody, e.g., an antibody which binds specifically to the fusion junction.

Detection of the NDRG1-ERG fusion can be combined with detection of one or more other fusions associated with cancer such as prostate cancer, including, e.g., fusions between TMPRSS2 and ERG, and between SCL45A3 and ERG.

Compositions and kits containing one or more nucleic acid primers, probes, and antibodies, suitable for use in the detection of NDRG1-ERG fusion molecules are also provided.

In another aspect, the present invention provides isolated nucleic acids encoding an NDRG1-ERG fusion protein, and isolated NDRG1-ERG fusion polypeptides, as well as related expression vectors and host cells.

In a further aspect, the invention provides a method for identifying an agent useful for treating prostate cancer characterized by the presence of the NDRG1-ERG fusion. Such agent can be identified by screening for agents based on the ability to inhibit a biological function or reduce the level of an NDRG1-ERG fusion molecule in a cell which expresses the NDRG1-ERG fusion molecule. An example of a biological function of a NDRG1-ERG fusion protein is to enhance the invasion ability of the cell which expresses the NDRG1-ERG fusion protein.

In a further aspect, the invention provides a method for treating a patient having prostate cancer characterized by NDRG1-ERG fusion. Such method involves administration of an agent that inhibits a biological function or reduces the level of a NDRG1-ERG fusion molecule.

BRIEF DESCRIPTION OF THE DRAWINGS

FIG. 4A. Nucleotide sequence (SEQ ID NO: 6) from NDRG1-ERG fusion cDNA, variant 1. The ERG portion is underlined.

FIG. 4B. Protein Sequence of NDRG1-ERG chimeric protein (SEQ ID NO: 7) encoded by NDRG1-ERG cDNA variant 1, with the ERG portion underlined.

FIG. 5A. Nucleotide sequence (SEQ ID NO: 8) from NDRG1-ERG fusion cDNA, variant 2. The ERG portion is underlined.

FIG. 5B. Protein Sequence of NDRG1-ERG chimeric protein (SEQ ID NO: 9) encoded by NDRG1-ERG cDNA variant 2, with the ERG portion underlined.

FIG. 11. Expression of NDRG1-ERG enhanced cell invasion. mRNA (top) and protein (middle) expression in the indicated cell lines following transient transfection of either NDRG1-ERGflag or NDRG1-ERG retroviral expression systems. Invasion assay (bottom) of HEK293 cells expressing LacZ control (left) or NDRG-1-ERG fusion (right) proteins.

DETAILED DESCRIPTION OF THE INVENTION

Figure 1A:
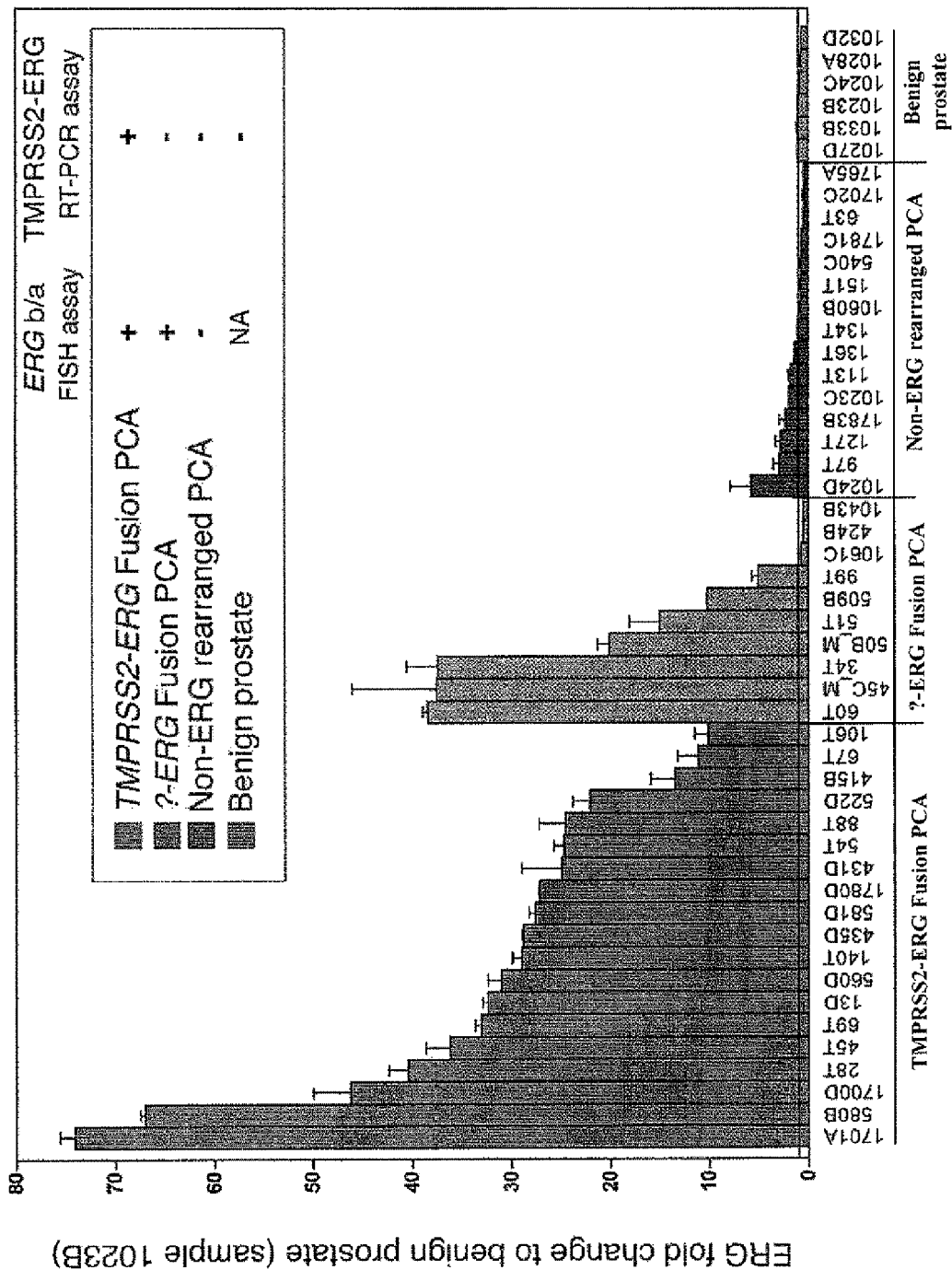
FIG. 1. ERG mRNA expression in prostate cancer and benign tissue. (A) Quantitative RT-PCR of ERG expression in 29 ERG rearranged (including 19 TMPRSS2-ERG mRNA positive (orange) and unknown mechanism-ERG (?-ERG, green)), 15 ERG non-rearranged (blue) and 6 benign prostate tissue samples (gray). (B) Exon composition and sequence (SEQ ID NO: 3) covering the fusion junction of SLC45A3-ERG transcript. (C) FISH images of nuclei with SLC45A3 rearrangement (upper) and SLC45A3-ERG fusion (lower) nucleus with yellow fusion signal.

The present inventors have identified a novel gene fusion associated with cancers including prostate cancer. More specifically, a novel gene fusion has been identified in prostate cancer over-expressing ERG, which fusion involves NDRG1 (N-myc downstream regulated gene 1) and ERG (v-ets erythroblastosis virus E26 oncogene homolog). The NDRG1-ERG gene fusion is inducible by androgen and by estrogen, and encodes a fusion-specific protein. Accordingly, the present invention provides compositions and methods useful for diagnosing and treating cancer including prostate cancer characterized by the NDRG1-ERG fusion.

NDRG1-ERG Fusion Molecules

A "NDRG1-ERG fusion molecule", as referred to herein, can be a chimeric nucleic acid molecule (genomic DNA, cDNA, and RNA) or a chimeric protein molecule.

Without being bound to any particular theory, it is believed that the fusion between NDRG1 and ERG results from chromosomal rearrangement or translocation which brings together a 5' portion of the NDRG1 gene and a 3' portion of the ERG gene, normally located on separate chromosomes, a create a chimeric gene at one chromosomal location (i.e., a genomic fusion molecule).

While the junction of the genomic fusion molecule may vary, the 5' portion of the NDRG1 gene that constitutes the genomic fusion molecule typically includes a portion from the 5' transcription regulatory region of the NDRG1 gene. By "5' transcription regulatory region", it is meant the region upstream of the transcription start site of a gene that controls transcription of the gene, which includes a promoter, a TATA box in many cases, and possibly one or more of other regulatory elements (e.g., an enhancer). In addition to a portion from the 5' transcription regulatory region of the NDRG1 gene, the genomic fusion molecule can also include one or more exons and introns from the 5' region of the NDRG1 gene or portions thereof.

The 3' portion of the ERG gene that constitutes the genomic fusion molecule typically includes a portion from the 3' region of the ERG gene, for example, the 3' region of the ERG gene coding for the 3' untranslated sequence of an ERG mRNA or a portion thereof, one or more exons or introns from the 3' region of the ERG gene or portions thereof.

Transcription of a genomic NDRG1-ERG fusion molecule produces a NDRG1-ERG fusion transcript (i.e., chimeric mRNA). A NDRG1-ERG fusion transcript is composed of a 5' portion of an NDRG1 mRNA, joined 5' to a 3' portion of an ERG mRNA.

The 5' portion of an NDRG1 mRNA that constitutes a fusion transcript typically includes the 5' un-translated region of an NDRG1 mRNA. By "5' un-translated region" it is meant the region of an mRNA that starts at the +1 position (i.e., where transcription begins) and ends just before the start codon of the coding region. The fusion transcript can also include full length or portions of one or more exons from 5' of an NDRG1 mRNA.

By a "portion" of an exon, it is meant a contiguous sequence of an exon that is shorted than the entire length of the exon. Generally speaking, a portion of an exon can be at least 5, 10, 15, 20, 25, 30, 35, 40 nucleotides or more in length.

There are several NDRG1 transcription splice variants and ERG transcription splice variants in human. The cDNA sequence of human NDRG1 transcription variant 2 and the locations of its exons are illustrated in SEQ ID NO: 1.

In one embodiment, the fusion transcript includes at least exon 1 of an NDRG1 mRNA, or a portion of exon 1. In another embodiment, the fusion transcript includes at least exon 1 and exon 2 or a portion of exon 2 of an NDRG1 mRNA. In still another embodiment, the fusion transcript includes at least exon 1, exon 2, and exon 3 or a portion of exon 3 of an NDRG1 mRNA.

The 3' portion of an ERG mRNA that constitutes a fusion transcript may include the 3' un-translated region transcribed from the ERG gene. The 3' un-translated region is the section of an mRNA that follows the coding region and is not translated. The 3' un-translated region is typically followed by a poly-A tail. The fusion transcript can also include full length or portions of one or more exons from 3' of an ERG mRNA. Several transcription splice variants have been reported for human ERG. The cDNA sequence of human ERG transcription variant 3 and the locations of its exons are illustrated in SEQ ID NO: 2. The exons in this variant are numbered in SEQ ID NO: 2 consecutively, consistent with the report by Wang et al. (*Cancer Res.* 2006 Sep. 1; 66(17):8347-51).

The junction of a NDRG1-ERG fusion transcript may vary, which may result from variations in the junction of NDRG1-ERG fusion at the genomic level, or alternatively from variations in transcription splicing from a genomic fusion molecule. Two NDRG1-ERG fusion transcript variants have been identified in accordance with the invention, as described in details in the following examples. cDNA sequences derived from these mRNA variants which include the exons and the junction of the fusion are depicted in FIGS. 4A and 5A, and set forth in SEQ ID NOS: 6 and 8, respectively.

Upon translation, the fusion transcripts produce fusion proteins. The two NDRG1-ERG fusion transcript variants identified herein are found to encode and produce chimeric NDRG1-ERG fusion proteins, the sequences of which are depicted in FIGS. 4B and 5B, and set forth in SEQ ID NOS: 7 and 9, respectively.

Cancer Diagnosis

According to the present invention, diagnosis of cancer in a subject is based on detection of the NDRG1-ERG fusion. The methods provided by the present invention are applicable to diagnosing cancer, including but not limited to prostate, breast, colon, pancreas, and lung cancers. In one specific embodiment, the methods are directed to diagnosis of prostate cancer.

The term "subject" being tested includes all mammalian subjects, particularly human subjects.

The term "diagnosis" or "diagnosing" is meant a determination that the subject has cancer or likely has cancer. The diagnostic method based on detection of NDRG1-ERG fusion molecules can be combined with other diagnostic tests to reduce false positive or false negative results.

Diagnosis of cancer can be based on detection of the presence of a fusion molecule, either a genomic fusion molecule, a fusion transcript, a fusion protein, or a combination thereof. In some embodiments, detection of the presence of a fusion molecule in a sample, e.g., observation of expected fluorescent signals in a break apart or fusion FISH assay, or observation of a signal in a nucleic acid hybridization or amplification-based assay or an immunoassay, is indicative of the presence of cancer. In other embodiments, the amount of a fusion molecule detected in a sample is quantified and compared to a control, and diagnosis is made based on an elevated level of the fusion molecule in the sample relative to the control. In still some other embodiments, the detection involves the use of reagents (e.g., primers, probes or antibodies specific for the junction of a fusion molecule) that permits a determination of the composition or identity of the fusion molecule.

By "control", it refers to the amount of fusion observed in a normal sample, such as sample from benign prostate tissue or normal non-prostate tissue, or urine or blood sample from a normal individual who does not have cancer.

By "elevated level" it is meant that the level is significantly increased as compared to control. A significant increase is meant an increase by at least 50%, 75%, 100% (twice the normal level), 2 fold, 3 fold, 4 fold, 5 fold, 6 fold, 7 fold, 8 fold, 9 fold, 10 fold, 11 fold, 12 fold, 13 fold, 14 fold, 15 fold, or greater.

Detection of fusion molecules can employ any suitable sample sources which include any biological specimen that contains fusion molecules for detection as described herein. Examples include tissue (such as prostate tissue), urine, blood, semen, prostatic secretions or prostate cells. In a specific embodiment, a urine sample is collected immediately following a digital rectal examination (DRE), which often causes prostate cells from the prostate gland to shed into the urinary tract. Samples obtained from the above-identified sources can be further processed in order to enrich for the fusion molecules or cells containing the fusion molecules. The processing may include obtaining the serum or plasma portion of blood, obtaining the supernatant or cell pellet portion of urine, homogenization of tissue, lysis of cells, among others, in order to provide materials suitable for assaying the fusion molecules.

Detection of fusion molecules in a sample can be achieved by using a variety of techniques documented in the art. Fusion nucleic acid molecules can be detected by using various nucleic acid-based techniques, including hybridization (such as solution-phase hybridization, in situ hybridization (ISH), e.g., fluorescent ISH (FISH); microarray, Northern blot and Southern blot), amplification (such as polymerase chain reaction (PCR), reverse transcription polymerase chain reaction (RT-PCR), transcription-mediated amplification (TMA), ligase chain reaction (LCR), strand displacement amplification (SDA), and nucleic acid sequence based amplification (NASBA)), and sequencing. Fusion proteins can be detected based on a variety of assays known for detection of proteins, including, for example, SDS-gel analysis, immunoassays (such as immunoprecipitation, Western blot, ELISA, immunohistochemistry, immunocytochemistry, and flow cytometry).

In addition to detection based on samples obtained from a subject, fusion molecules in a subject can also be detected by employing in vivo imaging techniques including, e.g., radionuclide imaging; positron emission tomography (PET); computerized axial tomography, X-ray or magnetic resonance imaging method, fluorescence detection, and chemiluminescent detection.

In one embodiment, detection of NDRG1-ERG fusion is achieved by performing an in situ hybridization (ISH) assay. Generally speaking, an ISH assay uses a labeled DNA or RNA strand as a probe that binds to a specific DNA or RNA sequence in a portion or section of tissue (in situ), or the entire tissue (whole mount FISH). The probe can be labeled with an isotope, a fluorescent compound, an antigen or any other appropriate label. Sample cells and tissues are usually treated to fix the target nucleic acids in place and to allow for access of the probe. After exposing the sample cells or tissues to the probe under appropriate hybridization conditions, the excess probe is washed away, and the probe bound to the target molecule is located using autoradiography, fluorescence microscopy or immunohistochemistry, depending upon the nature of the label.

In a specific embodiment, detection of NDRG1-ERG fusion is achieved by performing a fluorescent in situ hybridization (FISH) assay using a fluorescent-labeled probe.

Figure 1C:
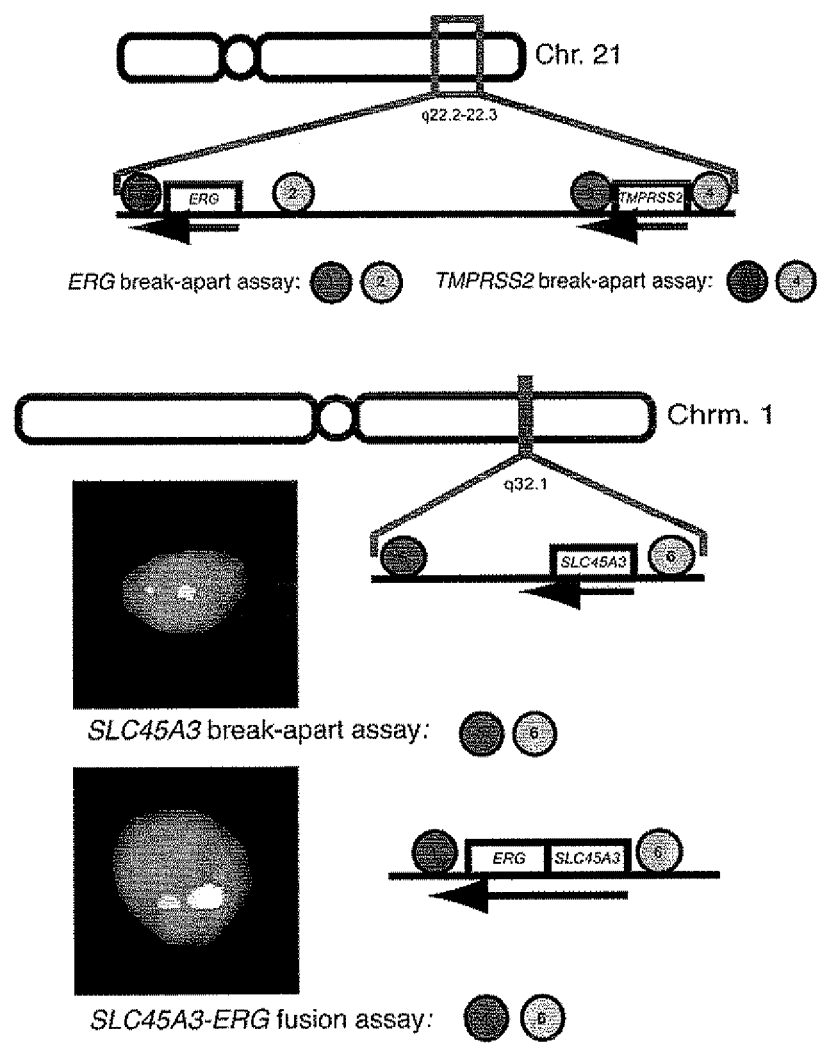
Figure 2A:
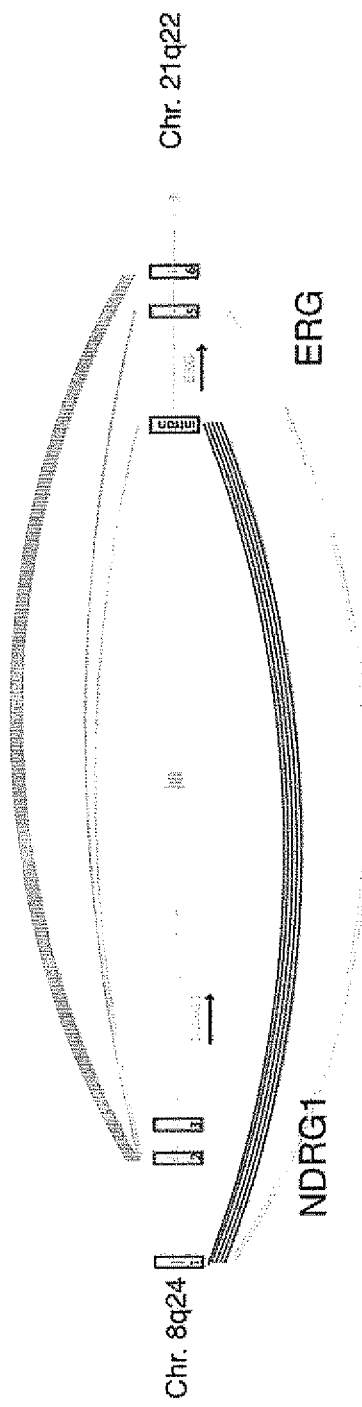
FIG. 2. Identification of NDRG1-ERG fusion by RNA sequencing. (A) The schematic shows the linear structure of NDRG1 and ERG. The gene representation shows the "union" transcripts, i.e. the exons of all isoforms are reported and, in the case of overlapping exons, the longest one is shown. Each arc represents one instance of paired reads where one read is mapped to NDRG1 and the other to ERG. The regions of the genes involved in the fusion transcript are highlighted and numbered. (B) RT-PCR products obtained using a forward primer targeting exon 1 of NDRG1 and a reverse primer targeting exon 6 of ERG (positive control:beta actin). Arrows indicate the DNA fragments that were isolated and sequenced. The lower portion provides sequence data from this analysis showing the NDRG1-ERG transcript exon composition and the sequence covering the fusion junction for the 2 variant mRNAs identified in samples 99_T (top, SEQ ID NO: 4) and 509_B (bottom, SEQ ID NO: 5). (C) Schematic of the FISH NDRG1 b/a and NDRG1-ERG fusion assays. (D) NDRG1 rearrangement (upper) indicated by separated red and green signals and NDRG1-ERG fusion (lower) indicated by an overlap of the red ERG and the green NDRG1 signal in a representative nucleus from case 99_T.
Figure 2B:
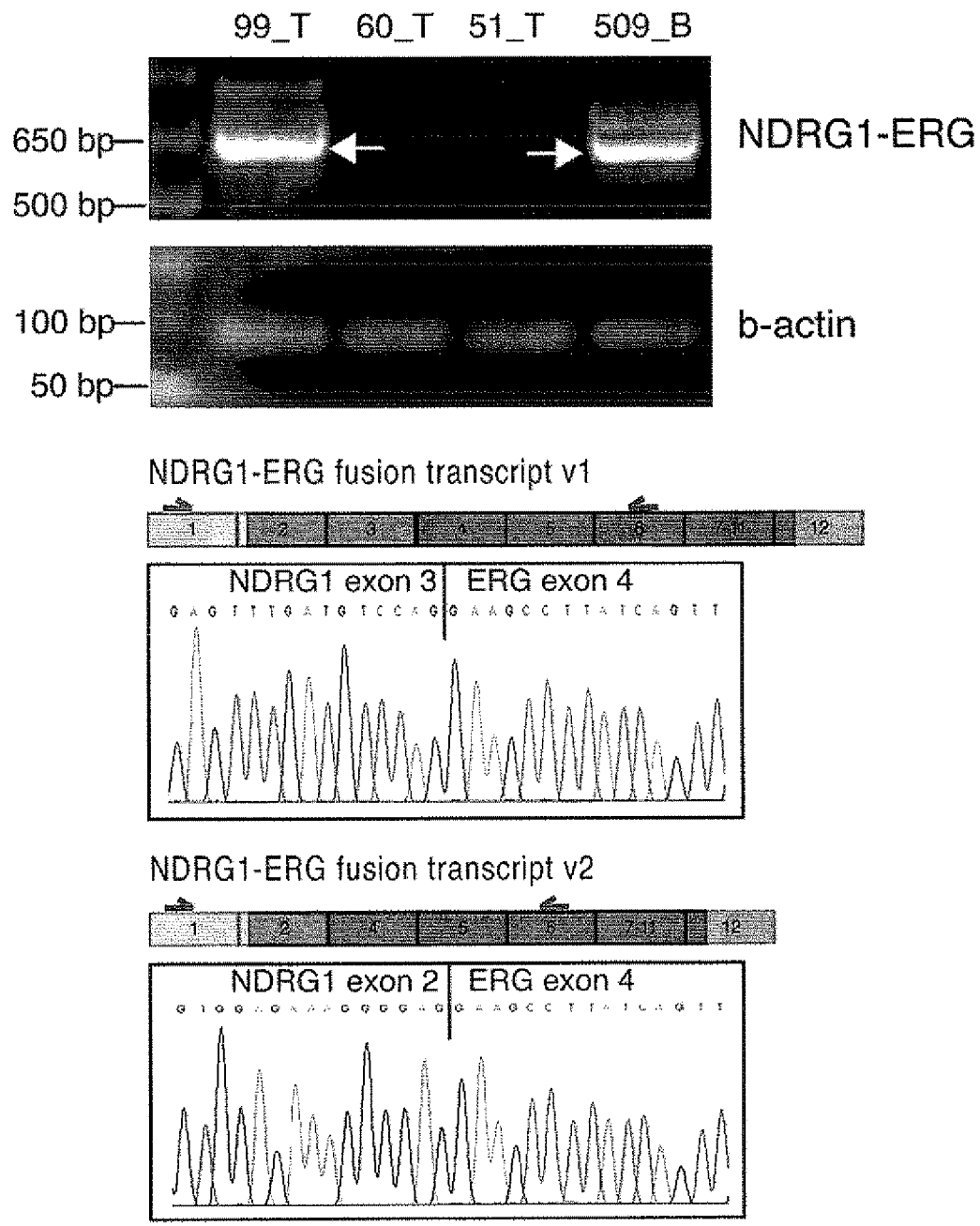
Figure 2C:
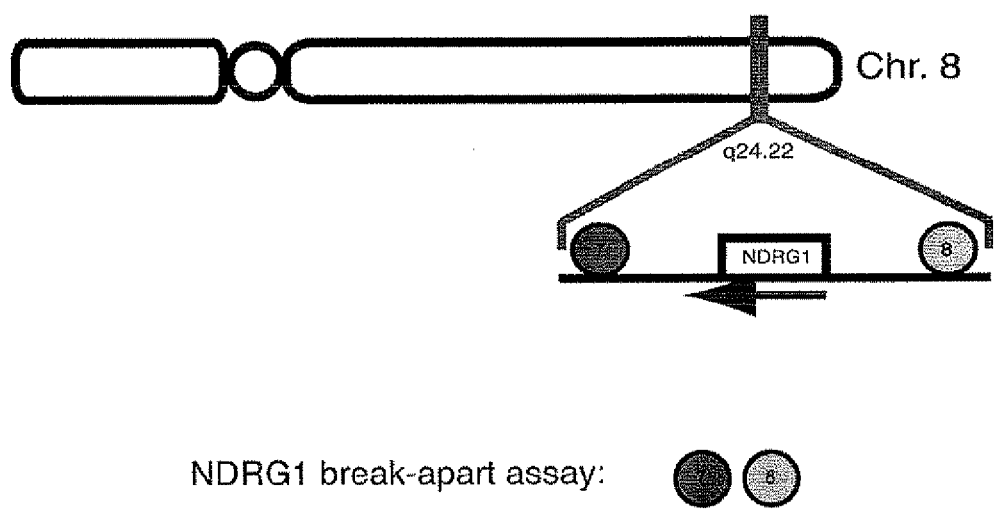

In specific embodiments, a break-apart FISH assay is performed for detection of translocation of a gene of interest. Such break-apart assay uses a pair of probes, as illustrated in FIGS. 1C and 2C. One of the probes specifically binds to a chromosomal region on the centromeric side of the gene of interest and is labeled to generate a first florescent color, and the other probe binds to a chromosomal region on the telomeric side of the gene of interest and is labeled to generate a second florescent color different from the first color. In preferred embodiments, the probes do not overlap with sequences of the gene of interest. With normal chromosomes without rearrangement of the gene of interest, juxtaposition or superimposition of the two colors is observed. On the other hand, the two colors will split and appear on separate derivative chromosomes in cases of a reciprocal translocation involving the gene of interest; or alternatively, a single color generated by the centromeric probe will appear in cases of a translocation with a deletion of the telomeric region.

In a specific embodiment, a break-apart FISH assay is performed for detection of translocation of the NDRG1 gene using a centrometic probe and a telomeric probe flanking the NDRG1 gene. Observation of a split of the fluorescent colors generated from the two probes is indicative of translocation of the NDRG1 gene, and hence the presence of cancer.

In other specific embodiments, a fusion FISH assay is performed for detection of a gene fusion. Such fusion FISH assay also uses a pair of probes, as illustrated in FIG. 1C. One of the probes specifically binds to a chromosomal region upstream of the 5' partner of the gene fusion and is labeled to generate a first florescent color, and the other probe binds to a chromosomal region downstream of the 3' partner of the gene fusion and is labeled to generate a second, different florescent color. With normal chromosomes without the gene fusion, the two colors will appear on separate derivative chromosomes; whereas juxtaposition or superimposition of the two colors will be observed if the gene fusion has occurred.

In a specific embodiment, a fusion FISH assay is performed for detection of the NDRG1-ERG fusion using a pair of probes. One of the probes specifically binds to a chromosomal region upstream of the NDRG1 gene and is labeled to generate a first florescent color, and the other probe binds to a chromosomal region downstream of the ERG gene and is labeled to generate a second, different florescent color. Observation of juxtaposition or superimposition of the two colors is indicative of the fusion and hence the presence of cancer.

In certain embodiments, FISH assays are performed using fluorescence-labeled bacterial artificial chromosomes (BACs) as probes. BAC clones containing specific BACs are available from distributors that can be located through many sources, e.g., National Center for Biotechnology Information (NCBI). Each BAC clone from the human genome has been given a reference name that unambiguously identifies such clone. These names can be used to find a corresponding GenBank sequence and to order copies of the clone from a distributor. Non-limiting examples of BAC clones suitable for use in the diagnostic methods of the invention are listed in Table 3.

In another embodiment, detection of NDRG1-ERG fusion is achieved by using a nucleic acid-amplification based technique. Both genomic DNA and mRNA can be obtained from a suitable sample and used as template in an amplification reaction, permitting detection of genomic fusion molecules and fusion transcripts.

For example, NDRG1-ERG genomic fusion molecules can be detected by PCR using primers including a first primer which is specific for a 5' region of the NDRG1 gene (for example, the 5' regulatory region, the genomic region encoding the 5' untranslated region of NDRG1 mRNA, exons in the 5' region such as exons 1, 2 or 3), and a second primer specific for a 3' region of the ERG gene (for example, exons in the 3' region such as exon 4 or any other downstream exon, the genomic region encoding the 3' untranslated region of ERG mRNA).

NDRG1-ERG fusion transcripts can be detected by RT-PCR using primers including a first primer which is specific for a 5' region of a NDRG1 mRNA (such as the 5' untranslated region, exons 1, 2 or 3), and a second primer specific for a 3' region of an ERG mRNA (such as exon 4 or any other downstream exon, and the 3' untranslated region).

When referring to an oligonucleotide primer or probe as "specific for" a region, it is meant that such primer or probe has sufficient identity with a sequence within the region or its complementary strand, such that the primer or probe specifically hybridizes to the sequence or its complementary strand under stringent conditions. Stringency is dictated by temperature, ionic strength, and the presence of other compounds such as organic solvents. For example, "high stringency conditions" can encompass hybridization at 42° C. in a solution consisting of 5× SSPE (43.8 g/l NaCl, 6.9 g/l NaH2PO4H2O and 1.85 g/l EDTA, pH adjusted to 7.4 with NaOH), 0.5% SDS, 5× Denhardt's reagent and 100 μg/ml denatured salmon sperm DNA, followed by washing in a solution comprising 0.1× SSPE, 1.0% SDS at 42° C. or higher (e.g., 55° C., 60° C. or 65° C.). "Medium stringency conditions" can encompass hybridization at 42° C. in a solution consisting of 5× SSPE with NaOH), 0.5% SDS, 5× Denhardt's reagent and 100 μg/ml denatured salmon sperm DNA followed by washing in a solution comprising 1.0× SSPE, 1.0% SDS at 42° C.

In some embodiments, NDRG1-ERG fusion transcripts are detected based on hybridization or amplification types of assays (such as RT-PCR, FISH, among others) that utilize a primer or probe specific for the junction of an identified fusion transcript variant, alone or in combination with primer or probe not specific to the junction. Junction-specific oligonucleotides are specific for the junction of a fusion nucleic acid, and permits differentiation of a fusion nucleic acid versus native nucleic acids (e.g., native NDRG1 or ERG gene or mRNA).

A junction-specific primer or probe can be designed based on the sequence surrounding the point of fusion between the NDRG1 portion and the ERG portion in a fusion variant. Generally speaking, a junction-specific oligonucleotide primer or probe should be at least about 14 or 15 nucleotides in length, or 16, 17, 18, 19, 20, 21, 22, 23, 24, 25 or more nucleotides in length. A junction-specific oligonucleotide primer or probe is designed to have sufficient identity to a junction such that it hybridizes specifically to the junction under stringent conditions, but not to native nucleic acids without fusion. In specific embodiments, a junction specific primer or probe includes at least 3, 5, 6, 7, 8, 9, 10, 11, or 12 nucleotides from either side of the point of junction. If a fusion junction contains one or more nucleotides that are common to the two joining nucleic acids, a junction-specific primer should include the shared or common nucleotide or nucleotides, and additionally, at least 3, 5, 6, 7, 8, 9, 10, 11, or 12 nucleotides from either side of the shared nucleotide(s). In other embodiments, especially for amplification-based detection, a junction-specific primer is designed to target more of the 5' partner of the fusion than the 3' partner to minimize hybridization of the primer to native, non-fusion NDRG1 or ERG mRNA. In other words, the primer has a bigger 5' portion that hybridizes to one side of the junction sequence than the 3' portion of the primer which hybridizes to the other side of the junction. For example, a junction specific primer of 18 nucleotides in length can include a 5' portion of 12-14 nucleotides that corresponds to one side of the junction sequence, and a 3' portion of 4-6 nucleotides that corresponds to the other side of the junction sequence.

In a further embodiment, NDRG1-ERG fusion is detected based on analysis of chimeric NDRG1-ERG proteins. For such detection, peptides can be synthesized based on the junction amino acid sequences of identified chimeric variants and used to generate antibodies which specifically recognize the chrimeric fusion protein, and not the native protein without fusion. Generally, a junction-specific peptide is at least 6 or 7 amino acids, preferably 8 or 9 amino acids, in length to be immunogenic. In some embodiments, a junction-specific peptide contains 7, 8, 9, 10, 12, 13, 14, 15, 16, or more amino acids of the junction of a fusion variant, and depending on the length of the peptide, may include at least 1, 2, 3, 4, 5, 6, 7, 8 or more amino acids from each side of the junction. In a specific embodiment, a junction-specific peptide includes at least 2 or 3 amino acids from each fusion partner. In other embodiments, full length chimeric NDRG1-ERG proteins or fragments thereof can be used as immunogens to generate antibodies, which are screened to identify those antibodies that only bind chimeric fusion proteins but not native NDRG1 or ERG protein.

In accordance with the present invention, detection of NDRG1-ERG fusion molecules can be combined with other tests in order to achieve more accurate diagnostic results. Other diagnostic tests include, for example, detection of other fusions associated with cancer, including gene fusions between TMPRSS2 and ERG, between SLC45A3 and ERG gene, as described in e.g., U.S. Published Application 2007/0212702. In the experiments described in the following examples, NDRG1-ERG fusion has been observed in prostate cancers overexpressing ERG yet negative for TMPRSS2 or SLC45A3 rearrangement. Accordingly, detection of NDRG1-ERG fusion molecules may provide a useful complement to other diagnostic tests based on fusion detection. For example, a multiplex panel can be utilized which detects TMPRSS2-ERG, SCL45A3-ERG and NDRG1-ERG fusions.

Drug Screening

In a further embodiment, the invention provides a method of screening for inhibitors of NDRG1-ERG fusion. Specifically, candidate compounds can be screened for their ability to reduce the level of expression or to inhibit a biological function of an NDRG1-ERG fusion molecule. The method can be performed in vitro using a cell line having elevated levels of a NDRG1-ERG fusion molecule, e.g., a cell line transfected to express an NDRG1-ERG fusion molecule. Candidate compounds can include nucleic acid molecules, small organic molecules, and antibodies, for example. The identified compound may reduce either the mRNA or the protein level of an NDRG1-ERG fusion molecule, or inhibiting a biological function of such fusion. Biological functions of NDRG1-ERG fusion proteins include, e.g., enhancing cell migration or cell invasion, which are properties frequently observed with cancerous cells. Cell invasion and cell migration can be assessed by using known assays and techniques, such as the Boyden chamber assay well documented in the art.

Cancer Treatment

The present invention also provides methods for treating cancers associated with NDRG1-ERG fusion, including but not limited to to prostate, breast, colon, pancreas, and lung cancers. By "treating" it is meant eliminating or at least inhibiting or reducing the growth or metastasis of cancerous cells. Treatment may also reduce or prevent the occurrence of cancer (e.g., in subjects predisposed to developing cancer associated with NDRG1-ERG fusion), or reduce or prevent reoccurrence of cancer associated with NDRG1-ERG fusion.

The treatment involves administration to a subject an agent that inhibits a biological function of a NDRG1-ERG fusion molecule, or reduces the level of the fusion molecule. The agent can be any one of a small molecule compound, an siRNA, an antisense nucleic acid, or an antibody, or a combination thereof.

In one embodiment, the treatment employs an inhibitor of an NDRG1-ERG fusion protein, e.g., a compound that inhibits a biological function (e.g., the function of conferring enhanced cell invasion potential) of an NDRG1-ERG fusion protein.

In another embodiment, the treatment employs an siRNA molecule. The term "siRNAs" refers to small interfering RNAs, which may include a double-stranded region of about 18-30, or 20-25 nucleotides. One strand of the double-stranded region is identical or substantially homologous to a target RNA molecule. The double-stranded region can be formed by two separate RNA strands, or a singled RNA molecule (e.g., a hairpin shape). In some embodiments, siRNAs are designed to target the junction region of a NDRG1-ERG fusion transcript.

Compositions and Kits

Isolated or recombinant NDRG1-ERG fusion nucleic acid molecules, including genomic DNA, mRNA and cDNA fusion molecules, are provided by the present invention. In one embodiment, the nucleic acid molecule encodes a chimeric NDRG1-ERG fusion protein. In a specific embodiment, the nucleic acid molecule encodes a chimeric NDRG1-ERG fusion protein having the amino acid sequence set forth in SEQ ID NO: 7 or SEQ ID NO: 9. Examples of such nucleic acid molecules include those having the nucleotide sequence as set forth in SEQ ID NO: 6 or SEQ ID NO: 8.

Isolated or recombinant NDRG1-ERG fusion proteins are also provided by the present invention. Examples of NDRG1-ERG fusion proteins include those having the amino acid sequence as set forth in SEQ ID NO: 7 or SEQ ID NO: 9.

Modified fusion nucleic acid or protein molecules, where one or more nucleotides or amino acids have been substituted, added or deleted, are also contemplated by the invention, so long as the modified molecules are substantially identical to the fusion molecules prior to the modification. A substantial identity is measured by a substantial sequence identity (i.e., at least 75%, 80%, 85%, 90%, 95%, 98%, 99% or greater), or by substantial functional identity (i.e., the modified molecule retains at least 70%, 75%, 80%, 85%, 90%, 95%, or greater of a biological function of a fusion molecule prior to modification). Fusion molecules can also be modified to include additional features, such as labels or compounds capable of generating a detectable signal, additional sequences corresponding to an epitope tag or a restriction endonuclease site, among others.

The invention also provides expression vectors for expressing a chimeric NDRG1-ERG fusion protein in a host cell. Such expression vectors contain a nucleic acid which encodes a chimeric NDRG1-ERG fusion protein, and the coding sequence of the chimeric protein is operably linked to a promoter at 5', and to a termination sequence at 3'. Any promoter which can direct the expression of a chimeric NDRG1-ERG protein in a desirable host cell can be used, and can be a constitutive or inducible promoter, including e.g., the native human NDRG1 promoter. Numerous promoters suitable for directing expression in bacterial, fungal or mammalian cells have been documented in the art.

Host cells transformed with any such expression vector are also provided by the invention. Suitable host cells include any bacterial, fungal, and mammalian cells suitable for propagation of the expression vector or recombinant expression of fusion molecules.

In additional embodiments, the present invention provides oligonucleotide primers and probes, peptides, and antibodies, useful for practicing the diagnostic methods described herein. One or more such components or reagents can be provided in a diagnostic kit.

Oligonucleotide primers or probes suitable for use in the detection, whether specific for a fusion junction or otherwise, can include additional features in addition to the sequence binding region, such as a sequence that does not bind to the junction sequence (e.g., a tag sequence or a promoter sequence) and does not interfere with binding to the intended target sequence in the junction. The primers or probes can also include non-nucleic acid moieties such as labels that do not interfere with target binding.

Similarly, peptides or antibodies, whether specific for a fusion junction or otherwise, can include additional features, such as additional amino acids that are not part of a fusion protein, labels, among others.

In the following examples, reference is made to the accompanying drawings that form a part hereof, and in which is shown by way of illustration specific embodiments which may be practiced. These embodiments are described in detail to enable those skilled in the art to practice the invention, and it is to be understood that other embodiments may be utilized and that changes may be made without departing from the scope of the present invention. The following description of exemplified embodiments is, therefore, not to be taken in a limited sense.

EXAMPLES

Example 1

Analysis of ERG Overexpression in Prostate Cancer Prostatectomy Samples

Prostate cancer prostatectomy samples from 101 men were screened for ERG gene rearrangement using a FISH break-apart (b/a) assay. In total, 44 cases were positive for ERG rearrangement. Given the heterogeneity of TMPRSS2-ERG mRNA expression level (as reported by Wang et al., *Cancer Res*, 66, 8347-51, 2006) in prostate cancer, TMPRSS2-ERG mRNA variant expression was screened using conventional RT-PCR and DNA sequencing. Of the 44, 34 (77%) expressed 7 different variants of TMRPSS2-ERG mRNA described by Wang et al. (2006), supra. In order to determine the level of ERG mRNA over-expression, quantitative PCR was performed using cDNA from 29 cases (19 that were TMRPSS2-ERG mRNA positive and 10 TMPRSS2-ERG mRNA negative), 15 cases that did not show ERG rearrangement and 6 benign prostate tissue samples (FIG. 1A). ERG mRNA was over-expressed up to 75 times (median of 27) in ERG rearranged cases compared to baseline levels in benign prostate tissue and cases negative for both ERG rearrangement and TMPRSS2-ERG mRNA. Contrary to findings by Wang et al. (2006), supra, TMPRSS2-ERG mRNA isoform expression was not associated with ERG over-expression or with prostate cancer progression (Gleason score, pathologic stage, or surgical margin status, as shown in Table 1).

TMPRSS2-ERG mRNA was absent in 10 (23% of 44) ERG rearranged cases, of which 7 expressed high ERG mRNA levels (5-38 times). To confirm the absence of TMPRSS2 rearrangement in these cases, a TMPRSS2 b/a FISH assay was performed. TMPRSS2 rearrangement was observed in 2/10 cases (60T and 51T), indicating a novel TMPRSS2-ERG fusion that was not detected using standard RT-PCR approaches. To screen for other possible fusion events with ERG, RT-PCR analysis was performed targeting known ETS family fusion partners (SLC45A3, HERV-K, C15ORF21, HNRPA2B1, DDX5, CANT1, KLK2 and ACSL3). This screening revealed that exon 4 of ERG was fused to exon 1 of SLC45A3 in 3 ERG mRNA over-expressed cases (34T, 150B_M, 145C_M, FIG. 1B). The predicted open reading frame is identical to what is encoded by the most common TMPRSS2 (exon 1)-ERG (exon 4) mRNA transcript. This was confirmed in-situ using SLC45A3 and ERG b/a-assays and an SLC45A3-ERG fusion assay (FIG. 1C).

Patient information, the materials and methods used in the above experiments are as follows.

Patient Population—The study is composed of 101 men with localized and locally advanced prostate cancer who underwent radical prostatectomy as a monotherapy. All prostate cancer cases were collected as part of institutional review board—approved research protocols.

Sample processing for RNA Analyses—Hematoxylin and eosin slides were prepared from formalin-fixed paraffin-embedded material and evaluated for cancer extent and tumor grade (Gleason score). Hematoxylin and eosin slides were prepared from the corresponding frozen tissue block and evaluated for the extent of cancer involvement. To ensure for a high concentration of cancer cells and minimized benign tissue, tumor isolation was performed by first selecting for high-density cancer foci (<10% stromal and other nontumor tissue contamination) and then taking 1.5-mm tissue cores from the frozen tissue block for RNA extraction. Sections for fluorescence in situ hybridization (FISH) evaluation were taken from the frozen tissue block used for molecular analysis. The cancer foci selected for RNA extraction were well characterized by FISH to evaluate the ERG rearrangement status throughout the entire focus. Special care was taken to extract the RNA from a single cancer focus to exclude the problem of heterogeneity when looking for putative fusion transcripts. RNA was isolated from frozen tissue using TRIzol LS reagent (lnvitrogen, Carlsbad, Calif.) according to the manufacturer's instructions. After DNase treatment (Invitrogen), RNA concentration was measured using a NanoDrop 8000 spectrophotometer (Thermo Scientific, Wilmington, Del.), Quality was assessed using the Bioanalyzer 2100 (Agilent Technologies, Inc, Santa Clara, Calif.). The qualitative detection of fusion transcripts in the cases was performed using conventional reverse transcription—polymerase chain reaction (RT-PCR), agarose gel fractionation/purification, and subsequent complementary DNA (cDNA) sequencing. For this amplified DNA, fragments corresponding to the expected sizes of fusion transcripts were gel-extracted using the MinElute Gel Extraction Kit (Qiagen) and sequenced at the Q4 Life Sciences Core Laboratories Center's DNA sequencing facility of Cornell University (Ithaca, N.Y.). Quantitative ERG and TMPRSS2-ERG RT-PCR was performed using QuantiTect SYBR Green PCR Kit (Qiagen). Each sample was run in duplicate. The amount of each target gene relative to a control gene was determined using the comparative Ct method (ABI Bulletin 2; Applied Biosystems). Ct values Q5 for ERG were first normalized using the average Ct values obtained for SART3 and TCFL1/VPS72 and then calibrated using normalized Ct values obtained from benign prostate. The protocols and primers for all RT-PCR assays used are shown in Table 2.

Figure 2D:
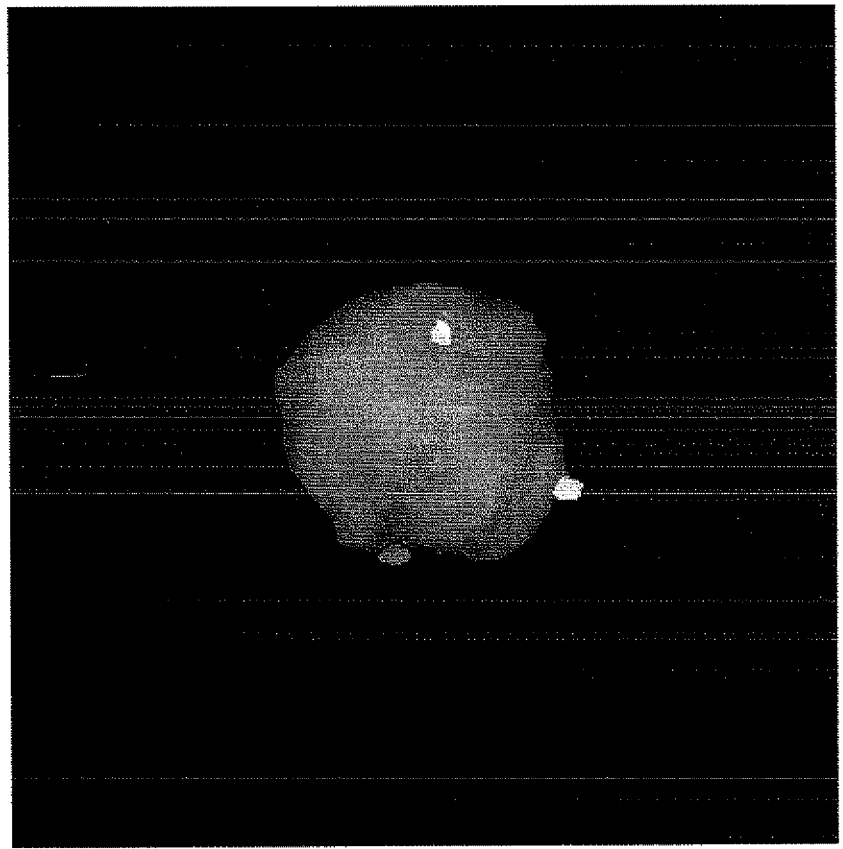
Figure 3:
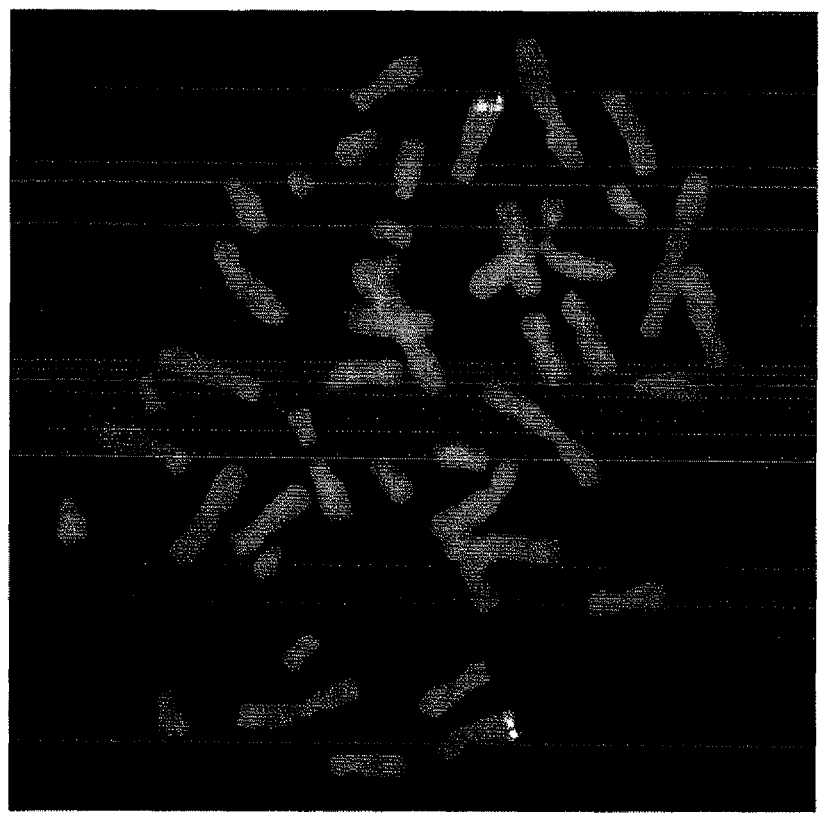
FIG. 3. Representative image of a metaphase spread from normal human male lymphocytes displaying the correct chromosome 8q24.22 position of FISH BAC probes targeting the NDRG1 locus used in the b/a assay.

Assessment of ERG, TMPRSS2, SLC45A3 and NDRG1 Rearrangements Using Two-Color FISH Assays—To assess for rearrangement of ERG, TMPRSS2, SLC45A3 and NDRG1, break-apart (b/a) FISH assays (essentially as described by Penner et al., *Am J Surg Pathol,* 31, 882-8, 2007) were performed on sections from the corresponding frozen tissue blocks. For designing a FISH break-apart assay, the inventors tested 5-10 Bacterial Artificial Chromosomes (BAC) probes flanking a gene of interest (GOI) on the centromeric side and 5-10 BAC probes flanking the telomeric side of the GOI, ideally not overlapping with sequences of the GOI. The BAC probes were hybridized on metaphase spreads of fixed cells to evaluate their target sequence specificity and selectivity (correct chromosomal location and no cross-hybridization to other chromosomes), fluorescence signal intensity and compatibility with the hybridization protocol. The probes which best matched all these requirements were selected for the assay. The centromeric probes for ERG, TMPRSS2, SLC45A3 and NDRG1 were RP11-24A11, RP11-354C5, RP I1-249H15 and RP11-185E14, respectively. The telomeric probes for ERG, TMPRSS2, SLC45A3 and NDRG1 were RP11-372O17, RP11-891L10, RP11-131E5 and RP11-1145H17, respectively. Probes RP11-131E5 (SLC45A3) and RP11-24A11 (ERG) were used for the SLC45A3-ERG fusion assay. Additional information regarding these probes is provided in Table 3. Correct chromosomal probe localization was confirmed on normal lymphocyte metaphase preparations, as exemplified in FIG. 3 which displays metaphase results for BACs targeting the NDRG1 locus. For each sample a minimum of 100 nuclei were analyzed. The b/a assays used for ERG, TMPRSS2 and SLC45A3 are schematically represented in FIG. 1C and that for NDRG1 is shown in FIGS. 2C-2D.

TABLE 1

ERG rearrangements, Over-Expression, TMRPSS2-ERG mRNA Variants and Clinical Information of Prostatectomy Samples Analyzed

| sample ID | ERG rearrangement | TMPRSS2-ERG isoform | ERG expression | Gleason score | Stage | Surgical margin | Seminal vesicle invasion |
|---|---|---|---|---|---|---|---|
| 1701_A | + | III | 74.04 | 3 + 4 | 3a | − | − |
| 580_B | + | III, VI | 66.97 | 3 + 4 | 2c | − | − |
| 1700_D | + | III | 46.18 | 4 + 4 | 3a | + | − |
| 28_T | + | III | 40.40 | 3 + 4 | 2c | − | − |
| 45_T | + | III, VI | 36.20 | 2 + 3 | 2c | + | − |
| 69_T | + | III, VI | 32.98 | 4 + 3 | 3a | − | − |
| 13_D | + | III | 32.35 | 3 + 3 | 2c | − | − |
| 560_D | + | III, VI | 30.96 | 4 + 3 | 3a | − | − |
| 140_T | + | II | 28.91 | 3 + 4 | 3a/b | − | + |
| 435_D | + | III | 28.75 | 3 + 4 | 3a | − | − |
| 581_D | + | III | 27.56 | 4 + 5 | 3b | − | + |
| 1780_D | + | III, VI | 27.10 | 3 + 4 | 2c | − | − |
| 431_D | + | III, VI | 24.92 | 3 + 3 | 2 | − | − |
| 54_T | + | III | 24.69 | 3 + 4 | 2c | + | − |
| 88_T | + | III | 24.52 | 3 + 5 | 3b | − | + |
| 522_D | + | IV | 22.06 | 3 + 4 | 2c | − | − |
| 415_B | + | III | 13.46 | 4 + 5 | 3a | − | − |
| 67_T | + | II, III, VI, VIII | 11.08 | 3 + 4 | 2c | − | − |
| 106_T | + | I, V | 10.06 | 3 + 5 | 3b | − | + |
| 60_T | + | — | 38.40 | 3 + 4 | 2c | + | − |
| 145_C_M | + | — | 37.54 | 4 + 5 | 3a | − | − |
| 34_T | + | — | 37.37 | 3 + 4 | 3b | − | + |
| 150_B_M | + | — | 20.06 | 2 + 3 | 2c | − | − |
| 51_T | + | — | 15.01 | 3 + 4 | 3a | − | − |
| 509_B | + | — | 10.12 | 3 + 4 | 2a | − | − |
| 99_T | + | — | 5.07 | 3 + 3 | 3a | + | − |
| 1061_C | + | — | 0.75 | 4 + 3 | 2c | − | − |
| 424_B | + | — | 0.53 | 3 + 4 | 2c | − | − |
| 1043_B | + | — | 0.50 | 3 + 3 | 2c | − | − |
| 1024_D | − | — | 5.74 | 4 + 5 | 3b | − | + |
| 97_T | − | — | 2.93 | 2 + 3 | 2c | − | − |
| 127_T | − | — | 2.72 | 3 + 3 | 2a | − | − |
| 1783_B | − | — | 2.26 | 4 + 4 | 2c | − | − |
| 1023_C | − | — | 1.97 | 3 + 3 | 2c | − | − |
| 113_T | − | — | 1.77 | 4 + 5 | 3b | + | + |
| 136_T | − | — | 1.36 | 3 + 3 | 3a | + | − |
| 134_B | − | — | 1.04 | 3 + 2 | 2b | + | − |
| 1060_B | − | — | 0.79 | 4 + 3 | 2c | − | − |
| 151_T | − | — | 0.77 | 2 + 3 | 2c | − | − |
| 540_C | − | — | 0.74 | 3 + 4 | 3a | − | − |
| 1781_C | − | — | 0.71 | 3 + 4 | 2c | + | − |
| 63_T | − | — | 0.45 | 2 + 4 | 2c | − | − |
| 1702_C | − | — | 0.43 | 3 + 4 | 3a | − | − |
| 1765_A | − | — | 0.41 | 3 + 4 | 2a | + | − |
| 1027_D | na | — | 1.07 | na | na | na | na |
| 1033_B | na | — | 1.04 | na | na | na | na |
| 1023_B | na | — | 1.04 | na | na | na | na |
| 1024_C | na | — | 0.90 | na | na | na | na |
| 1028_A | na | — | 0.76 | na | na | na | na |
| 1032_D | na | — | 0.73 | na | na | na | na |

TABLE 3

| Gene | centromeric probe (labeled with red fluorescence) | | | telomeric probe (labeled with green fluorescence) | | |
|---|---|---|---|---|---|---|
| ERG | RP11-24A11 | Chromosome:<br>Start:<br>End:<br>Length:<br>Strand:<br>Score:<br>Bands: | chr21<br>39546498<br>39733869<br>187372<br>+<br>1000<br>21q22.13-21q22.2 | RP11-372O17 | Chromosome:<br>Start:<br>End:<br>Length:<br>Strand:<br>Score:<br>Band: | chr21<br>40367344<br>40557436<br>190093<br>+<br>1000<br>21q22.2 |
| TMPRSS2 | RP11-354C5 | Chromosome:<br>Start:<br>End:<br>Length:<br>Strand:<br>Score:<br>Bands: | chr21<br>42439601<br>42635437<br>195837<br>+<br>1000<br>21q22.2-21q22.3 | RP11-891L10 | Chromosome:<br>Start:<br>End:<br>Length:<br>Strand:<br>Score:<br>Band: | chr21<br>43409124<br>43594929<br>185806<br>+<br>1000<br>21q22.3 |
| SLC45A3 | RP11-249H15<br>based on hg18 | Chromosome:<br>Start:<br>End:<br>Length:<br>Band: | chr1<br>203724624<br>203787895<br>63271<br>1q32.1 | RP11-131E5<br>based on hg18 | Chromosome:<br>Start:<br>End:<br>Length:<br>Band: | chr1<br>203910487<br>204074037<br>163550<br>1q32.1 |
| NDRG1 | RP11-185E14 | Chromosome:<br>Start:<br>End:<br>Length:<br>Strand<br>Score<br>Band: | Chr8<br>134024919<br>134198328<br>173410<br>–<br>1000<br>8q24.22 | RP11-1145H17 | Chromosome:<br>Start:<br>End:<br>Length:<br>Strand:<br>Score:<br>Band: | Chr8<br>134333724<br>134466739<br>133016<br>+<br>1000<br>8q24.22 |

TABLE 2

Oligonucleotide primers and cycling conditions for RT-PCR assays.

| Assay | Gene | Accession number | Bases | Exon(s) | Primer |
|---|---|---|---|---|---|
| TMPRSS2-ERG exon 4 | TMPRSS2<br>ERG | NM_005656.2<br>NM_004449.3 | -4-17<br>276-252 | 1<br>5 | TMPRSS2-ERG_f<br>Exon4_r1 |
| TMPRSS2-ERG exon 6 | TMPRSS2<br>ERG | NM_005656.2<br>NM_004449.3 | -4-17<br>659-636 | 1<br>7 | TMPRSS2-ERG_f<br>ERG_Exon 5-6_r |
| TMPRSS2-ERG exon 9 | TMPRSS2<br>ERG | NM_005656.2<br>NM_004449.3 | -4-17<br>945-928 | 1<br>10 | TMPRSS2-ERG_f<br>ERG_Exon10_r |
| TMPRSS2-ERG exon 12 | TMPRSS2<br>ERG | NM_005656.2<br>NM_004449.3 | -4-17<br>1575-1549 | 1<br>13 | TMPRSS2-ERG_f<br>ERG_Exon13_r |
| ERG qPCR | ERG<br>ERG<br>SART3<br>SART3<br>TCFLI/VPS72<br>TCFLI/VPS72 | NM_004449.3<br>NM_004449.3<br>NM_014706.3<br>NM_014706.3<br>NM_005997.1<br>NM_005997.1 | 574-597<br>659-636<br>635-658<br>889-866<br>778-801<br>948-927 | 6-7<br>7<br>2<br>4<br>6<br>6 | ERG_Exon 5-6_f<br>ERG_Exon 5-6_r<br>SART3_f<br>SART3_f<br>TCFL1/VPS72_f<br>TCFL1/VPS72_r |
| TMPRSS2-ERG qPCR | TMPRSS2<br>ERG<br>HMBS<br>HMBS | NM_005656.2<br>NM_004449.3<br>NM_000190.3<br>NM_000190.3 | -4-17<br>276-252<br>711-730<br>790-772 | 1<br>5<br>10<br>11 | TMPRSS2-ERG_f<br>Exon4_r1<br>HMBS_f<br>HMBS_r |
| SLC45A3-ERG | SLC45A3<br>ERG<br>ERG | NM_033102.2<br>NM_004449.3<br>NM_004449.3 | 74-91<br>659-636<br>945-928 | 1<br>7<br>10 | SLC45A3_f<br>ERG-Exon 5-6_r<br>ERG_Exon10_r |
| HERV-K-ERG | HERV-K_22q11.23<br>ERG<br>ERG | BC020811.1<br>NM_004449.3<br>NM_004449.3 | 305-327<br>659-636<br>945-928 | n/a<br>7<br>10 | HERV-K_f<br>ERG_Exon 5-6_r<br>ERG_Exon10_r |
| HNRPA2B1-ERG | HNRPA2B1<br>ERG<br>ERG | NM_002137.2<br>NM_004449.3<br>NM_004449.3 | 136-155<br>659-636<br>945-928 | 1<br>7<br>10 | HNRPA2B1_f<br>ERG-Exon 5-6_r<br>ERG_Exon10_r |

TABLE 2-continued

| | | | | | |
|---|---|---|---|---|---|
| C15ORF21-ERG | C15ORF21 | NM_001005266 | 313-336 | 3 | C15ORF21_f |
| | ERG | NM_004449.3 | 659-636 | 7 | ERG_Exon 5-6_r |
| | ERG | NM_004449.3 | 945-928 | 10 | ERG_Exon10_r |
| CANT1-ERG | CANT1 E1a | n/a | n/a | n/a | CANT1 E1a_f |
| | ERG | NM_004449.3 | 659-636 | 7 | ERG-Exon 5-6_r |
| | ERG | NM_004449.3 | 945-928 | 10 | ERG_Exon10_r |
| CANT1-ERG | CANT1 E1 | NM_138793.2 | 48-65 | 1 | CANT-E1_f |
| | ERG | NM_004449.3 | 659-636 | 7 | ERG_Exon 5-6_r |
| | ERG | NM_004449.3 | 945-928 | 10 | ERG_Exon10_r |
| KLK2-ERG | KLK2 | NM_005551.3 | 65-77 | 1 | KLK2_f |
| | ERG | NM_004449.3 | 659-636 | 7 | ERG_Exon 5-6_r |
| | ERG | NM_004449.3 | 945-928 | 10 | ERG_Exon10_r |
| DDX5-ERG | DDX5 | NM_004396.2 | 423-443 | 3 | DDX5_f |
| | ERG | NM_004449.3 | 659-636 | 7 | ERG_Exon 5-6_r |
| | ERG | NM_004449.3 | 945-928 | 10 | ERG_Exon10_r |
| NDRG1-ERG | NDRG1 | NM_006096.2 | 30-53 | 1 | NDRG1_ex1_f |
| | ERG | NM_004449.3 | 659-636 | 7 | ERG-Exon 5-6_r |
| | ERG | NM_004449.3 | 945-928 | 10 | ERG_Exon10_r |
| | ERG | NM_004449.3 | 1575-1549 | 13 | ERG_Exon13_r |
| ERG 5'RACE | ERG | mRNA | 601-578 | 6-7 | ERG_GSP1 |
| | ERG | NM_004449.3 | 571-552 | 6 | ERG_GSP2 |
| | ERG | NM_004449.3 | 470-448 | 6 | ERG_GSP3 |

| Oligonucleotide primers and cycling conditions for RT-PCR assays. | | | |
|---|---|---|---|
| Assay | Gene | Sequence 5' -> 3' | cycling |
| TMPRSS2-ERG exon 4 | TMPRSS2 | TAGGCGCGAGCTAAGCAGGAG | 94° C. 2 min; 94° C. 30 s; 63° C. 30 s; 72° C. 1 min, 10 s; 72° C. 10 min 35 cycles |
| | ERG | GTAGGCACTCAAACAACGACTGG | |
| TMPRSS2-ERG exon 6 | TMPRSS2 | TAGGCGCGAGCTAAGCAGGAG | 94° C. 2 min; 94° C. 30 s; 63° C. 30 s; 68° C. 2 min; 68° C. 10 min 40 cycles |
| | ERG | CCATATTCTTTCACCGCCCACTCC | |
| TMPRSS2-ERG exon 9 | TMPRSS2 | CGCAGAGTTATCGTGCGAGGAGAT | 94° C. 2 min; 94° C. 30 s; 55° C. 30 s; 68° C. 2 min; 68° C. 10 min 40 cycles |
| | ERG | CCATATTGTTTCAGCGCCCACTCC | |
| TMPRSS2-ERG exon 12 | TMPRSS2 | TAGCGCGAGCTAAGCAGGAG | 94° C. 2 min; 94° C. 30 s; 55° C. 30 s; 68° C. 2 min; 68° C. 10 min 40 cycles |
| | ERG | TTAGTAGTAAGTGCCCAGATGAGAAGG | |
| ERG qPCR | ERG | CGCAGAGTTATCGTGCCAGCAGAT | 50° C. 2 min; 95° C. 15 min; 94° C. 1 min; 50° C. 1 min; 72° C. 1 min 41 cycles Melting curve; 70-90° C. every 0.2° C. for 1 s |
| | ERG | CCATATTCTTTCACCGCCCACTCC | |
| | SART3 | GCCCGCCAGAAGATGAGTGAAATC | |
| | SART3 | ACCAACAGACGAGAGAGCCCTTTC | |
| | TCFLI/VPS72 | ATTGACTCCTCATGCTGGGACTGG | |
| | TCFLI/VPS72 | CGGTATAGGGCTGGACGATGGG | |
| TMPRSS2-ERG qPCR | TMPRSS2 | TAGGCGCGAGCTAAGCAGGAG | 50° C. 2 min; 95° C. 15 min; 94° C. 1 min; 50° C. 1 min; 72° C. 1 min 41 cycles melting curve; 70-90° C. every 0.2° C. for 1 s |
| | ERG | GTAGGCACACTCAAACAACGACTGG | |
| | HMBS | CCATCATCCTGGCAACAGCT | |
| | HMBS | GCATTCCTCAGGGTGCAGG | |
| SLC45A3-ERG | SLC45A3 | CGCTGGCTCCGGGTGACA | 94° C. 2 min; 94° C. 30 s; 55° C. 30 s; 68° C. 2 min; 68° C. 10 min 40 cycles |
| | ERG | CCATATTCTTTCACCGCCCACTCC | |
| | ERG | CGACTGGGGCGTGGGGTG | |
| HERV-K-ERG | HERV-K_22q11.23 | GTCCCAAGTACGTCCACGGTCAG | 94° C. 2 min; 94° C. 30 s; 55° C. 30 s; 68° C. 2 min; 68° C. 10 min 40 cycles |
| | ERG | CCATATTCTTTCACCGCCCACTCC | |
| | ERG | CGACTGGGGCGTGGGGTG | |
| HNRPA2B1-ERG | HNRPA2B1 | TGCGGGAAATCGGGCTGAAG | 94° C. 2 min; 94° C. 30 s; 55° C. 30 s; 68° C. 2 min; 68° C. 10 min 40 cycles |
| | ERG | CCATATTCTTTCACCGCCCACTCC | |
| | ERG | CGACTGGGGCGTGGGGTG | |
| C15ORF21-ERG | C15ORF21 | CAACTAACACTGCGGCTTCCTGAG | 94° C. 2 min; 94° C. 30 s; 55° C. 30 s; 68° C. 2 min; 68° C. 10 min 40 cycles |
| | ERG | CCATATTCTTTCACCGCCCACTCC | |
| | ERG | CGACTGGGGCGTGGGGTG | |

TABLE 2-continued

| | | | |
|---|---|---|---|
| CANT1-ERG | CANT1 E1a | GCTGGAGAAACAAACCCTCT | 94° C. 2 min; 94° C. 30 s; |
| | ERG | GCATATTCTTTCACCGCCCACTCC | 55° C. 30 s; 68° C. 2 min; |
| | ERG | CGACTGGGGCGTGGGGTG | 68° C. 10 min 40 cycles |
| CANT1-ERG | CANT1 E1 | AGCCAAGCCCCGCCGATC | 94° C. 2 min; 94° C. 30 s; |
| | ERG | CCATATTCTTTCACCGCCCACTCC | 55° C. 30 s; 68° C. 2 min; |
| | ERG | CGACTGGGGCGTGGGGTG | 68° C. 10 min 40 cycles |
| KLK2-ERG | KLK2 | TCTGTCCATCGGCTTGTCTGTG | 94° C. 2 min; 94° C. 30 s; |
| | ERG | CCATATTCTTTCACCGCCCACTCC | 55° C. 30 s; 68° C. 2 min; |
| | ERG | CGACTGGGGCGTGGGGTG | 68° C. 10 min 40 cycles |
| DDX5-ERG | DDX5 | AGAGGTCACAACTGCCCGAAG | 94° C. 2 min; 94° C. 30 s; |
| | ERG | CCATATTCTTTCACCGCCCACTCC | 55° C. 30 s; 68° C. 2 min; |
| | ERG | CGACTGGGGCGTGGGGTG | 68° C. 10 min 40 cycles |
| NDRG1-ERG | NDRG1 | CTGAAGCTCGTGAGTTCACCATCC | 94° C. 2 min; 94° C. 30 s; |
| | ERG | CCATATTCTTTCACCGCCCACTCC | 61° C. 30 s; 68° C. 2 min; |
| | ERG | CGACTGGGGCGTGGGGTG | 68° C. 10 min 40 cycles |
| | ERG | TTAGTAGTAAGTGCCCAGATGAGAAGG | |
| ERG 5'RACE | ERG | ATCCTAGACGACCGTGCTATTGAG | Reverse Transcription |
| | ERG | CGTTCGTGGTCATGTTTGGG | reaction at 55° C. 94° C. |
| | ERG | GCCACACTGCATTCATCAGGAGA | 2 min; 94° C. 30 s; 60° C. |
| | | | 1 min. 72° C. 1 min; 72° C. |
| | | | 7 min 35 cycles |
| | | | (45 cycles for GSP3-PCR) |

Example 2

Massively Parallel RNA-seq Discovers NDRG1-ERG Fusion

Having characterized all but two ERG over-expressing/ERG rearranged cases (509B, 99T), paired-end RNA-seq was used to identify potential 5' partners. Fusion transcripts were explored by looking for paired reads where each pair mapped to regions that were either greater than 2 MB apart and less than 5 MB apart, or mapped to different chromosomes (see Table 4). The utility of this approach was confirmed by limiting this analysis to matches with high numbers of reads. First, in prostate cancer cases known to harbor the TMPRSS2-ERG fusion (e.g., case 1701A), numerous TMPRSS2-ERG transcripts were detected. Second, SLC45A3-ELK4 transcript could also be detected in case 1701A as observed in an independent study. Finally, in 1 case (99T) with ERG over-expression but no SLC45A3 or TMPRSS2 rearrangement as determined by RT-PCR and FISH, RNA-sect demonstrated 17 copies of a fusion transcript that mapped paired reads to ERG exons and to exons of NDRG1 (FIG. 2A). This was confirmed by conventional RT-PCR (FIG. 2B). Sequence analysis of NDRG1-ERG cDNA (FIG. 4A, SEQ ID NO: 6) indicates that this fusion, as with BCR-ABL1 fusion gene in patients with chronic myeloid leukemia, encodes a chimeric protein containing 33 amino acids from NDRG1 as well as the conserved protein domains of wild type ERG (Sterile alpha motif/Pointed domain and ETS domain) (FIG. 4B, SEQ ID NO: 7). Screening other TMPRSS2-ERG, SLC45A3-ERG mRNA negative cases revealed another, slightly different, NDRG1-ERG transcript variant (variant 2) in 509B. NDRG1-ERG variant 2 mRNA (FIG. 5A, SEQ ID NO: 8) is also predicted to encode a chimeric protein including the first 21 amino acids of NDRG1 and the same conserved domains of ERG as in the protein encoded by NDRG1-ERG variant 1 (FIG. 5B, SEQ ID NO: 9). Sequences for NDRG1-ERG variant 1 and variant 2 have been submitted to GenBank (ace. #FJ627786 and #FJ627787). The chromosomal translocation which resulted in NDRG1-ERG fusion was confirmed at the genome level using an NDRG1 b/a and NDRG1-ERG fusion FISH assays (FIGS. 2C-2D).

RT-PCR analysis and b/a FISH assays were performed following the protocols described in Example 1. RNA-seq data analysis was performed as follows.

RNA Sequencing Data Analysis—The Illumina Genome Analyzer II was used for paired-end RNA sequencing. This provided a pair of approximately 30-36 base reads, from each end of a transcript fragment of relatively well-defined length (about 330 nucleotides). The paired reads were aligned independently to the human genome (hg18 assembly in the UCSC genome browser using "eland," a short-read alignment tool included in the Genome Analyzer software suite. For each read, eland provides the coordinate(s) of the alignment to the reference genome, allowing for up to two mis-matches in the sequence. Only the reads that are mapped uniquely to the genome were kept, although they might have up to two mis-matches. In order to search for novel translocations involving ERG, two strategies were applied. First, mapped paired reads were selected that were more than 2 MB and less than 5 MB apart. This allowed the identification of translocations similar to TMPRSS2-ERG in which the two genes are approximately 3 MB apart. Second, paired reads mapping to different chromosomes were also selected as potential candidates. Because the focus was on novel ERG partners, paired reads were selected where one of the reads lay within ERG. This allowed us to identify several candidate fusion transcripts spanning all chromosomes. Finally the chromosome with the highest number of reads was selected and checked if those reads lay within a gene.

TABLE 4

RNA-Seq Data

| Sample ID | # reads | # mappable reads | % mappable reads | Comments |
|---|---|---|---|---|
| 1701_A | 8,542,482 | 3,108,222 | 36.39% | (T2-ERG fusion positive) |

TABLE 4-continued

RNA-Seq Data

| Sample ID | # reads | # mappable reads | % mappable reads | Comments |
|---|---|---|---|---|
| 1783_B | 3,080,154 | 1,330,949 | 43.21% | (T2-ERG fusion negative) |
| 99_T | 2,844,879 | 1,180,781 | 41.51% | (NDRG1-ERG fusion positive) |

Example 3

TMPRSS2-, SLC45A3-, and NDRG1-ERG are Regulated by Androgen and Estrogen

Figure 6:
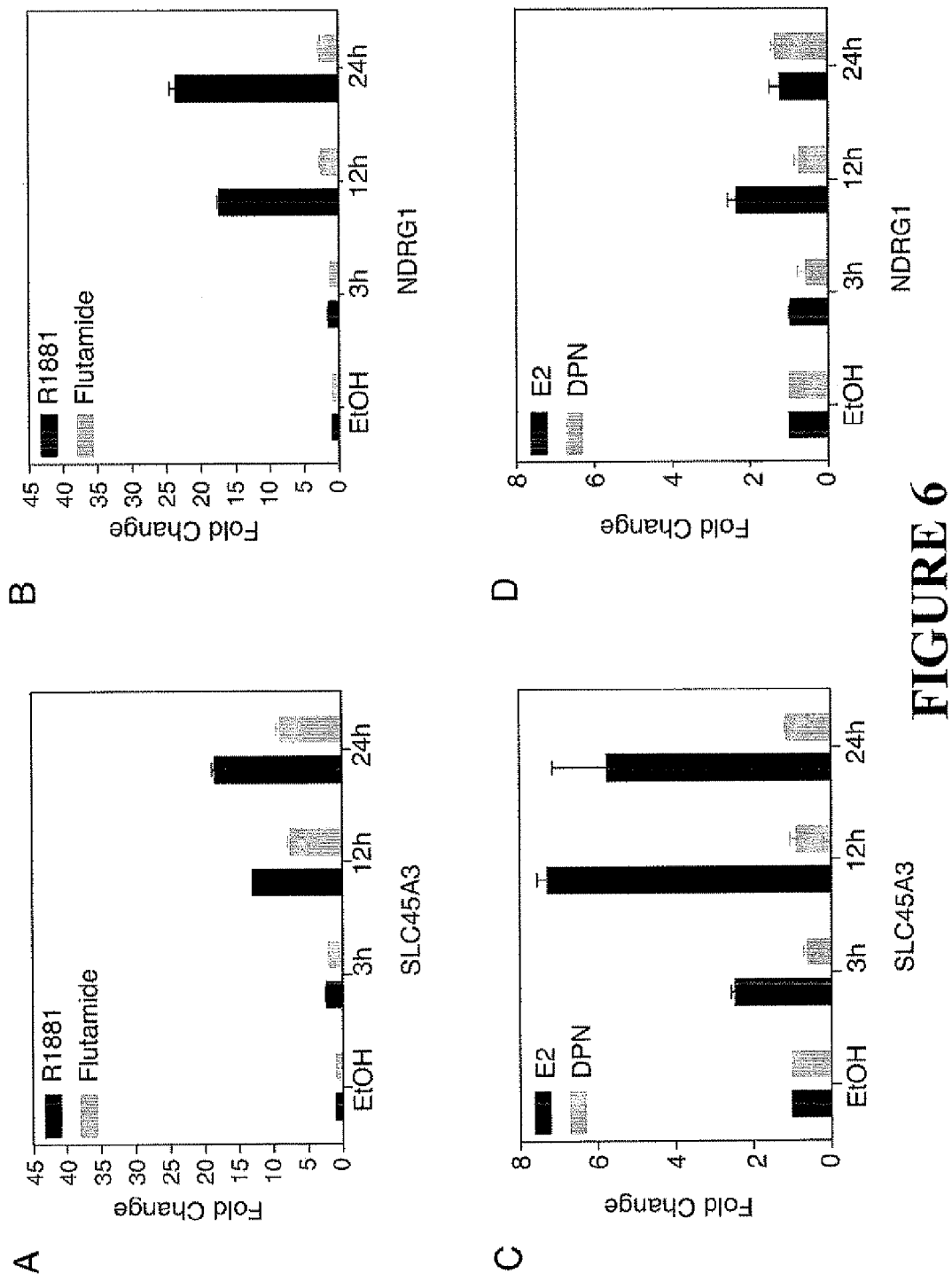
FIG. 6. Hormone treatment of LNCaP cells induced SLC45A3 and NDRG1 mRNA expression. SLC45A3 (A and C) or NDRG1 (B and D) mRNA expression was induced upon stimulation with synthetic androgen (R1881) and 17β-estradiol (E2). Serum-starved LNCaP cells were stimulated with 1 nM R1881, 1 nM R1881 in combination with 10 μM Flutamide (A and B), 10 nM E2 or 10 nM diarylpropionitrile (DPN) (C and D) for 3, 12 and 24 h. Samples were run in triplicate and normalized against TCFL1. Columns indicate the mean fold change of induction of three biological replicates against vehicle (Ethanol) only treated cells for the respective time points±SEM.

ERG mRNA expression in cases positive for SLC45A3-ERG or NDRG1-ERG is similar in magnitude to those measured for TMPRSS2-ERG positive cases. TMPRSS2 (Lin et al., Cancer Res, 59, 4180-4, 1999), SLC45A3 (Xu et al., Cancer Res, 61, 1563-8, 2001), and NDRG1 (Segawa et al., Oncogene, 21, 8749-58, 2002; Tu et al., Mol Cell Proteomics, 6, 575-88, 2007) are all known androgen induced genes. This was confirmed by treating LNCaP with a synthetic androgen (R1881, 1 nM) (FIGS. 6A-6B). Androgen regulation of NDRG1 is supported by the observation of an AR binding site ~30 kb upstream of the start site (chr8:134407748-134408779) in LNCaP cells. The induction of gene expression was abrogated in the presence of Flutamide. If KLK3 (PSA) mRNA was considered a surrogate read-out of androgen signaling, it would be expected to find similar profiles between PSA and ERG mRNA levels in TMPRSS2-ERG, SLC45A3-ERG or NDRG1-ERG mRNA positive prostate cancer cases. PSA mRNA levels, however, did not mimic the pattern of ERG mRNA levels in TMPRSS2-ERG, SLC45A3-ERG or NDRG1-ERG mRNA positive cases, indicating an additional mechanism for the regulation of the fusion transcripts.

Figure 7:
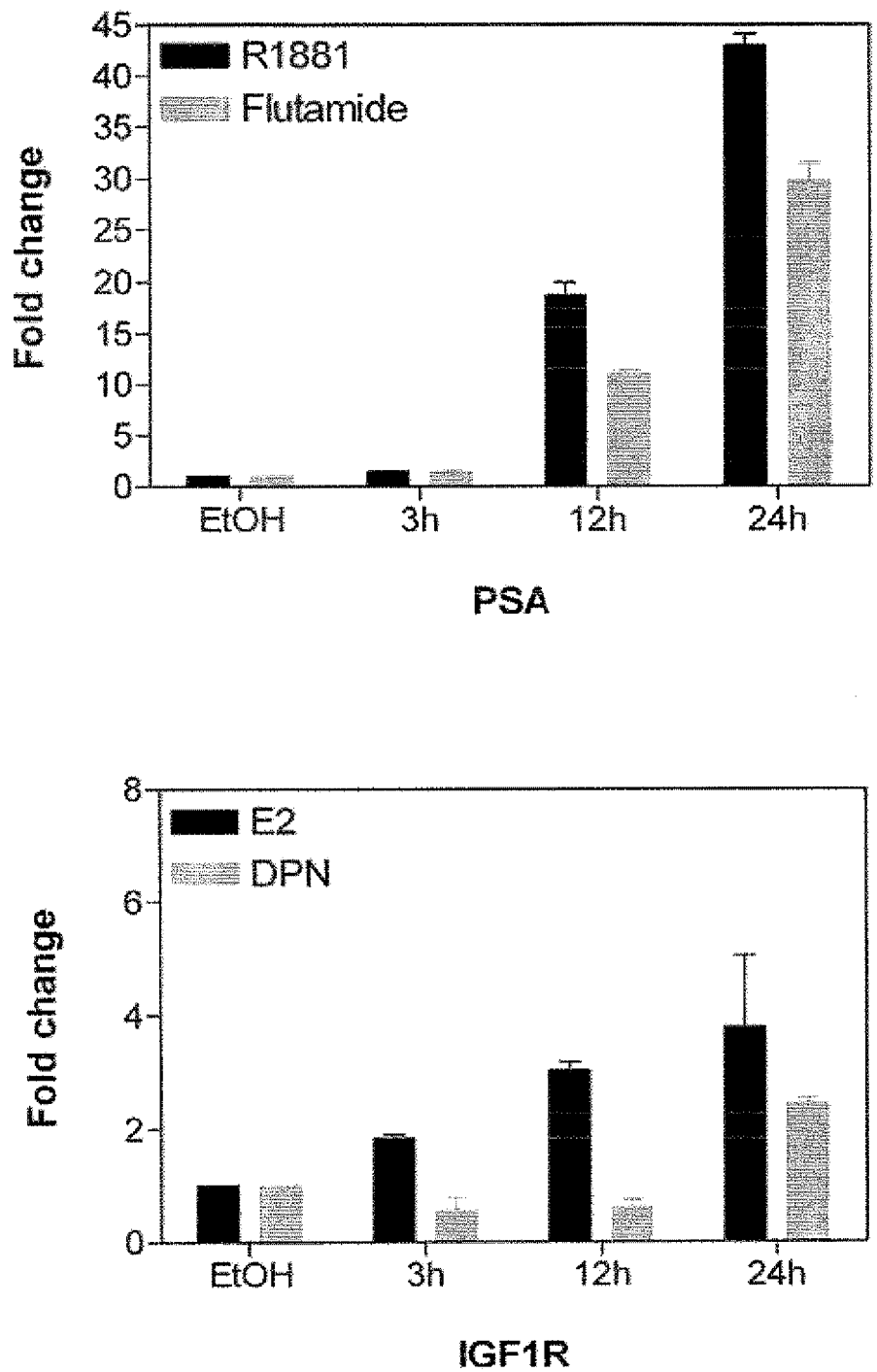
FIG. 7. Androgen and 17β-estradiol (E2) signaling of known target genes in LNCaP cells. IGF2R (A) and PSA (B) mRNA expression was induced upon stimulation with synthetic androgen (R1881) and E2. Serum-starved LNCaP cells were stimulated with 1 nM R1881, 1 nM R1881 in combination with 10 μM Flutamide, 10 nM E2 or 10 nM diarylpropionitrile (DPN) for 3, 12 and 24 h. Total RNA was extracted and used for quantitative RT-PCR using TAQMAN assay. Samples were run in triplicate and normalized against TCFL1. Columns indicate the mean fold change of induction of three biological replicates against vehicle (Ethanol) only treated cells for the respective time points±SEM.

TMPRSS2-ERG has been shown to be regulated by estrogen (Setlur et al., J Natl Cancer Inst, 100, 815-25, 2008). Chromosome-immunoprecipitation data indicates the presence of an estrogen receptor (ER) binding site within the SLC45A3 gene, an ER binding site in the first intron of NDRG1 (chr8:134373799-134375086) and at ~60 kb upstream of the start site (chr8:134441414-134442401). Similar data show that FoxA1, a known ER cofactor, binding sites overlap with the ER binding sites. To test this, the levels of SLC45A3 or NDRG1 mRNA in LNCaP cells were measured at different time points as a function of estrogen treatment. Induction of SLC45A3 mRNA and NDRG1 mRNA was observed at 3 hours (FIG. 6C) and 12 hours (FIG. 6D), respectively, following 17β-estradiol treatment, but not with the ERα receptor agonist DPN, similar to IGF1R mRNA, a known estrogen-induced gene in LNCaP cells (Pandini et al., Cancer Res, 67, 8932-41, 2007) (FIG. 7). This data indicate that, like TMPRSS2-ERG, SLC45A3-ERG and NDRG1-ERG fusion genes are also estrogen-regulated through ERα. This provides another mechanism for ERG over-expression when fused to SLC454A3 or NDRG1, particularly in the case of castrate-resistant prostate cancer.

Materials and methods used in the experiments of this Example are as follows.

Hormone Treatment of LNCaP—The prostate cancer cell line LNCaP was obtained from ATCC (Manassas, Va.; cat.#CRL-1740) and maintained according to the suppliers instructions. For hormonal treatment, cells were plated (500, 000 cells/10 cm$^2$) in the presence of complete growth medium supplemented with 1% Penicillin/Streptomycin. Cells were starved for 48 h in charcoal-stripped (CS) medium (RPMI-1640 1x, 5% charcoal-stripped PBS, 1% Penicillin/Streptomycin) and then treated with R1881 (1 nM), 17β-estradiol (10 nM), diarylpropionitrile (DPN, 10 nM) or ethanol vehicle for 3, 12, and 24 hours. RNA was extracted using the TRIzol Reagent (Invitrogen, Carlsbad, Calif.), subjected to DNase treatment (DNA-free™ Kit, Applied Biosystems) according to the manufacturer's instructions. To test for the specificity of androgen-stimulation, cells were treated with 10 μM Flutamide for 2 hours and then treated with R1881 as described above. TAQMAN expression assays (Applied Biosystems) were used to quantify relative levels of SL45A3, NDRG1, PSA (KLK3) and IGF1R. See Table 5.

TABLE 5

TAQMAN expression assays

| Gene | assay ID | reporter dye | location |
|---|---|---|---|
| SLC45A3 | Hs00263832_m1 | FAM | ex 5 |
| TCFL1 | Hs00195618_m1 | FAM | ex 6 |
| IGF1R | Hs99999020_m1 | FAM | ex 2 and 3 |
| KLK3 | Hs02576345_m1 | FAM | ex 1 and 2, detects all KLK3 transcript variants |
| NDRG1 | Hs00608387_m1 | FAM | ex 11 and 12 |

Expression profiling of ERG and 3 androgen-regulated genes—A subset of 65/101 samples were processed using Illumina HumanWG-6 v2.0 bead-arrays. A heatmap was constructed showing relative expression levels of ERG, TMPRSS2 and SLC45A3. The gene expression levels in a given sample have been color coded where orange to blue indicates high to low levels of expression. The samples have been grouped according to TMPRSS2-ERG (T2-ERG) fusion status as determined by RT-PCR and then ordered by the level of ERG microarray feature level normalized intensity.

Example 4

Expression of NDRG1-ERG Chimeric Protein Enhances Cell Invasion

Figure 8:
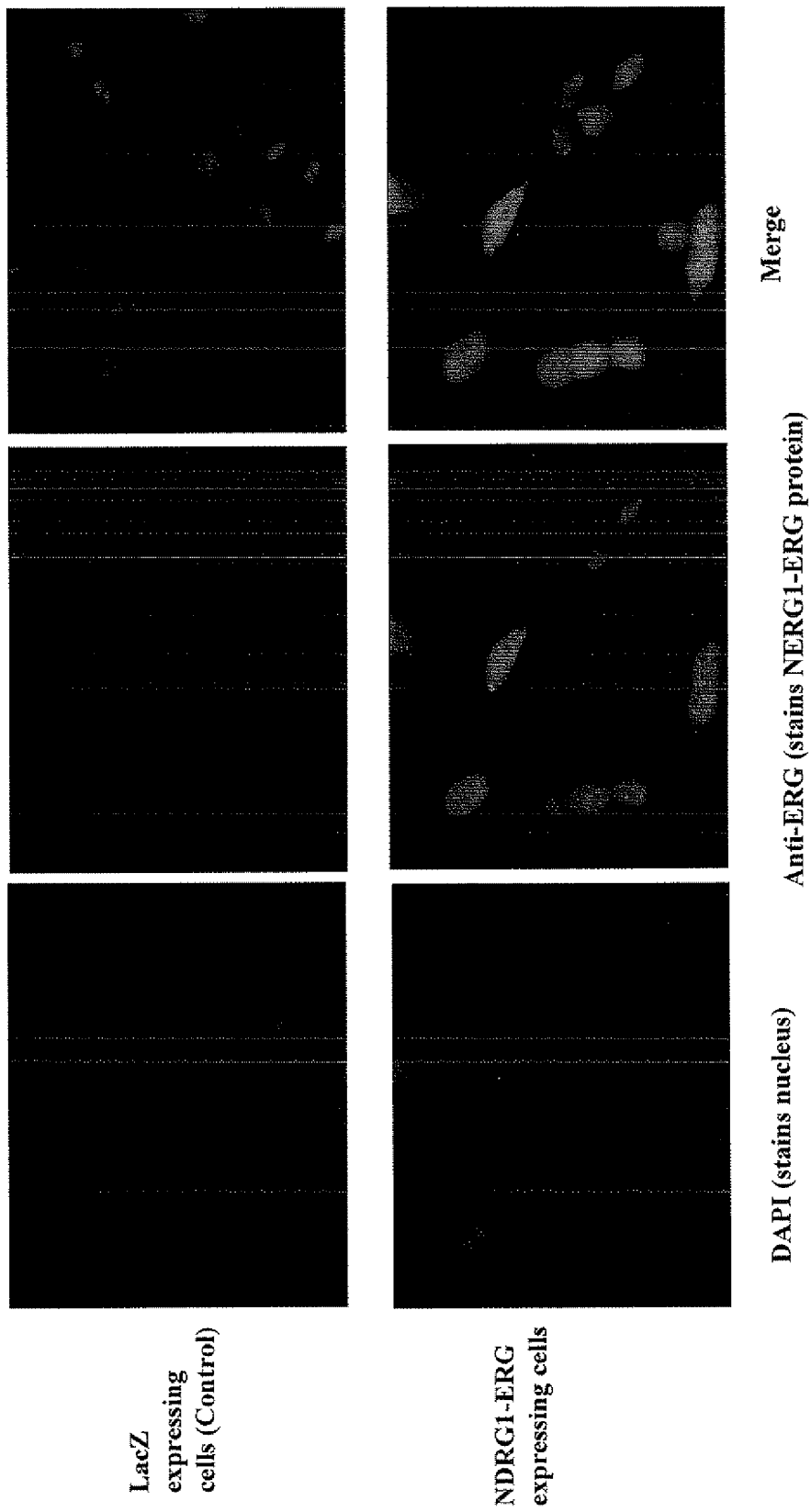
FIG. 8. NDRG1-ERG protein expression in HEK-293 (embryonic kidney) cells.
Figure 9:
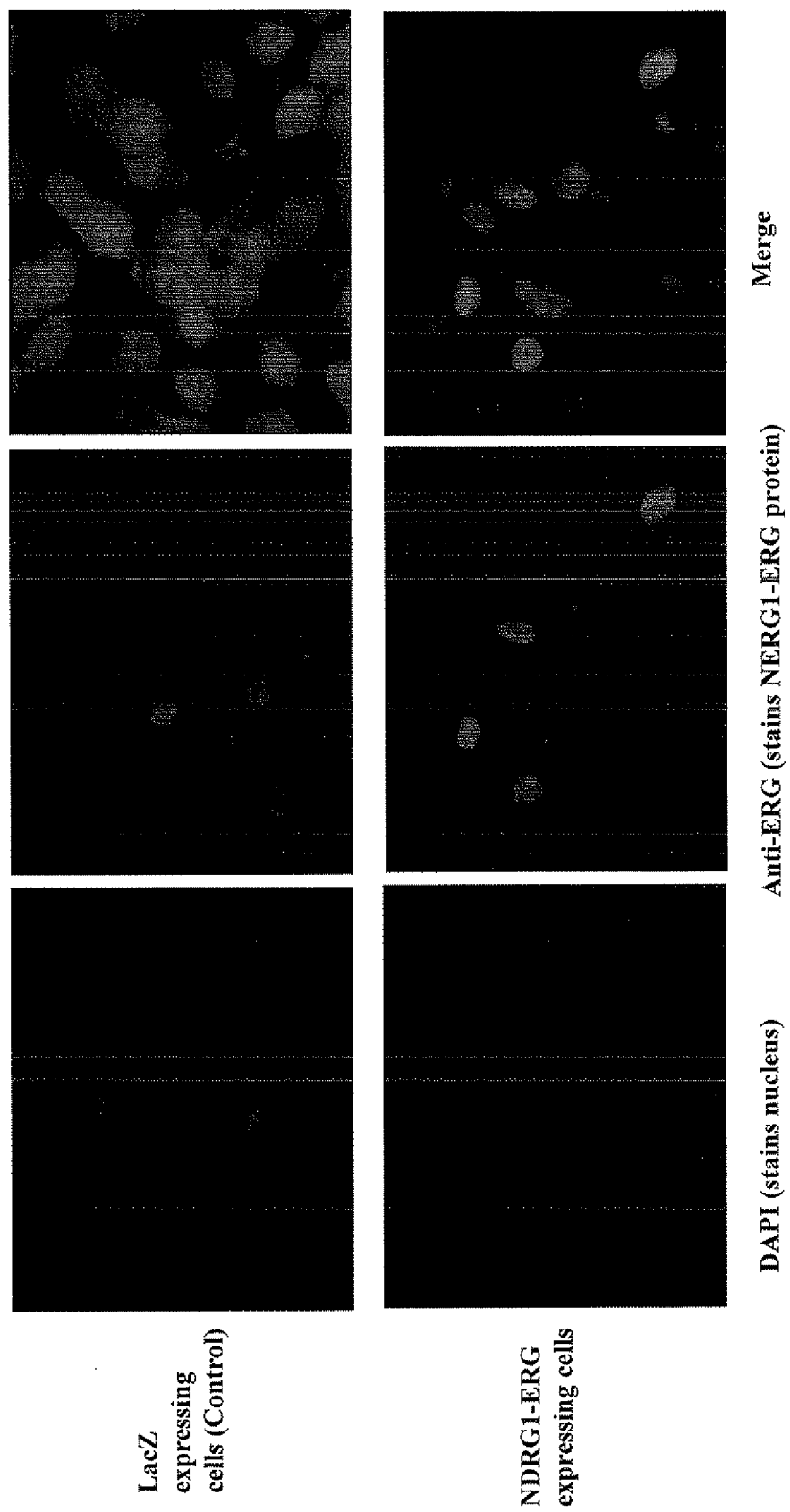
FIG. 9. NDRG1-ERG protein expression in BPH1 (prostate epithelial) cells.

HEK-293 (embryonic kidney) and BPH1 (prostate epithelial) cell lines were transiently transfected with a vector carrying the NDRG1-ERG fusion variant 1 cDNA. Expression of the NDRG1-ERG chimeric protein was observed by immunostaining the cells with an anti-ERG antibody, as shown in FIGS. 8-9.

Figure 10:
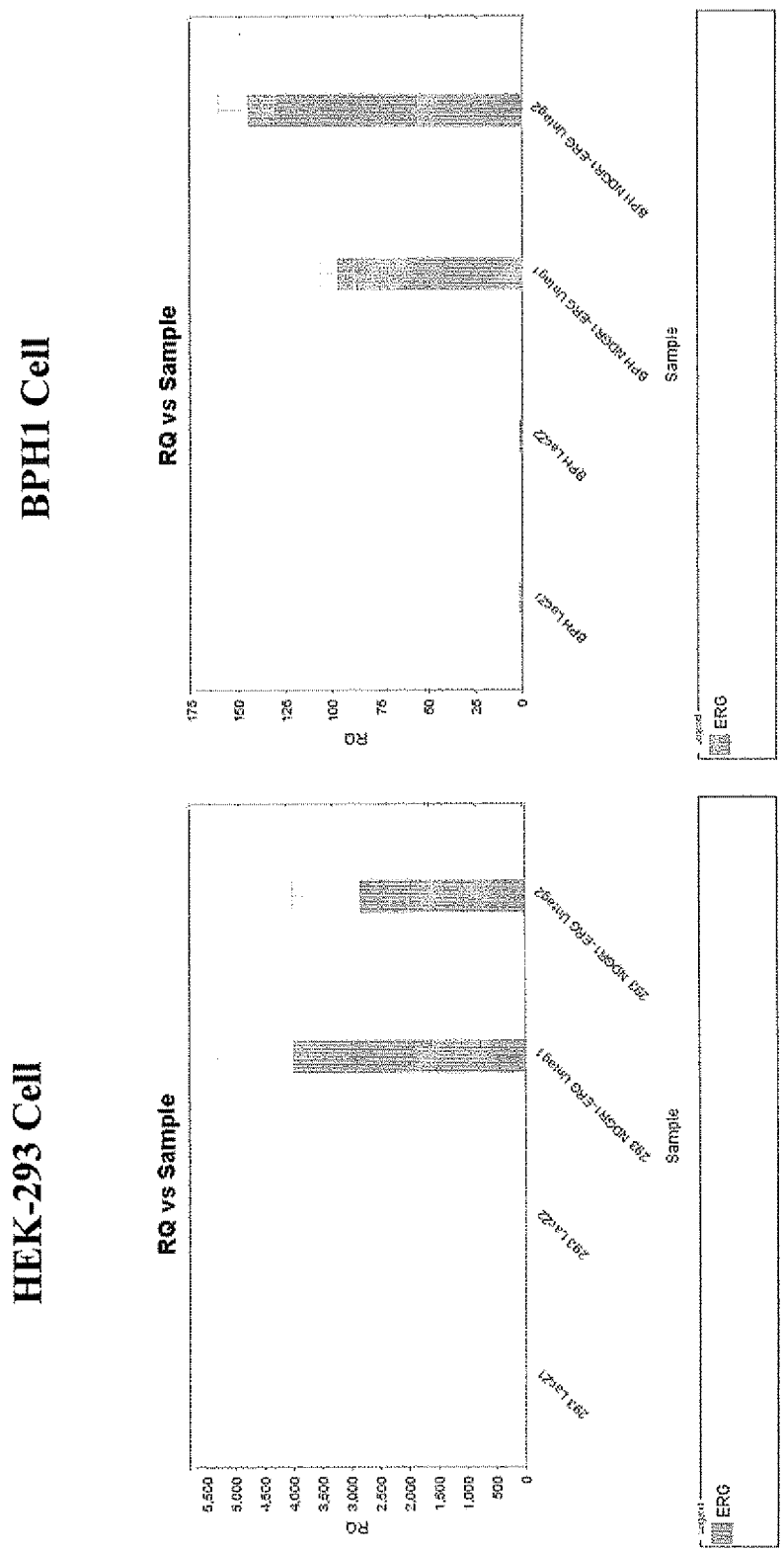
FIG. 10. NDRG1-ERG mRNA over-expression in HEK-293 and BPH1 cell lines. "RQ" stands for relative quantity.

Overexpression of the NDRG1-ERG mRNA in HEK-293 and BPH1 cell lines is shown in FIG. 10.

In a separate experiment, HEK-293 and BPH1 cell lines were transiently transfected with an NDRG1-ERGflag or NDRG1-ERG retroviral expression vector, or a vector expressing LacZ as control. The levels of mRNA in transfected HEK-293 cells were quantified (FIG. 11, top). Immunostaining of the transfected cells expressing NDRG1-ERGflag demonstrates that the chimeric NDRG1-ERG protein was produced in the cells (FIG. 11, middle). To assess the function of the chimeric protein, an invasion assay was performed using Boyden chambers coated with matrigel (BD Biosciences), with 10% fetal calf serum as chemoattractant, and HEK293 cells expressing LacZ control or NDRG-1-ERG fusion protein. As shown in FIG. 11, bottom, expression of the NDRG-1-ERG fusion protein enhanced cell invasion.

What is claimed is:

1. A method comprising providing a biological sample from a patient and detecting the presence of an NDRG1-ERG fusion molecule comprising a 5' portion of the NDRG1 gene and a '3 portion of the ERG gene in said sample, wherein the NDRG1-ERG fusion molecule being detected is a genomic fusion molecule on a chromosome comprising a 5' portion of the NDRG1 gene and a '3 portion of the ERG gene, wherein the 5' portion of the NDRG1 gene includes a portion of the 5' transcription regulatory region of the NDRG1 gene, wherein the genomic fusion molecule is detected by fluorescence in situ hybridization (FISH) assay selected from the group consisting of
   a) a FISH assay that detects translocation of NRGD1 using a pair of break-apart probes flanking the NDRG1 gene, wherein one probe is specific for a region on the centromeric side of the NDRG1 gene, and the other probe is specific for a region on the telomeric side of the NDRG1 gene, and
   b) a FISH assay that detects chromosomal rearrangement which creates an NDRG1-ERG fusion, wherein one probe is specific for the upstream chromosomal region of the NDRG1 gene, and the other probe is specific for the downstream chromosomal region of the ERG gene.

2. The method of claim 1, wherein the FISH assay is performed using a pair of break-apart probes flanking the NDRG1 gene, wherein one probe is specific for a region on the centromeric side of the NDRG1 gene, and the other probe is specific for a region on the telomeric side of the NDRG1 gene.

3. The method of claim 1, wherein the FISH assay is performed using a pair of probes that detect chromosomal rearrangement which creates an NDRG1-ERG fusion, wherein one probe is specific for the upstream chromosomal region of the NDRG1 gene, and the other probe is specific for the downstream chromosomal region of the ERG gene.

4. The method of claim 1, wherein the nucleic acid probes of (a) comprise BAC clones designated as RP11-185E14 and RP11-1145H17.

5. The method of claim 1, wherein nucleic acid probes of (b) comprise BAC clones designated as RP11-1145H17 and RP11-24A11.

6. A method comprising providing a biological sample from a patient and detecting the presence of an NDRG1-ERG fusion molecule comprising a 5' portion of the NDRG1 gene and a '3 portion of the ERG gene in said sample, wherein the NDRG1-ERG fusion molecule being detected is a fusion mRNA molecule comprising a 5' portion of an NDRG1 mRNA and a '3 portion of an ERG mRNA, wherein the NDRG1-ERG fusion molecule is detected by using a nucleic acid amplification method, using a first primer specific for a 5' region of an NDRG1 mRNA, and a second primer specific for a 3' region of an ERG mRNA wherein said fusion mRNA molecule is encoded by a cDNA comprising the nucleotide sequence of SEQ ID NO: 6 or SEQ ID NO: 8.

7. The method of claim 6, wherein the nucleic acid amplification method selected from the group consisting of polymerase chain reaction (PCR), and reverse transcription polymerase chain reaction (RT-PCR).

8. The method of claim 6, wherein said 5' region of the NDRG1 mRNA comprises the 5' untranslated region, exon 1, exon 2 and exon 3 of the NDRG1 mRNA.

9. The method of claim 8, wherein said first primer hybridizes to at least one of the 5' untranslated region or exon 1 of the NDRG1 mRNA.

10. The method of claim 6, wherein said 3' region of the ERG mRNA comprises the 3' untranslated region, exon 4 and exons downstream of exon 4.

11. The method of claim 6, wherein the nucleic acid amplification method is performed using primers comprising at least a primer specific for the junction of said fusion mRNA, wherein said junction comprises the sequence as set forth in SEQ ID NO: 4 or 5.

12. The method of claim 6, wherein said 5' region of the NDRG1 mRNA comprises the 5' untranslated region and exon 1 of the NDRG1 mRNA.

13. The method of claim 12, wherein said first primer hybridizes to at least one of the 5' untranslated region or exon 1 of the NDRG1 mRNA.

14. A method comprising providing a biological sample from a patient and detecting the presence of an NDRG1-ERG fusion molecule comprising a 5' portion of the NDRG1 gene and a '3 portion of the ERG gene in said sample, wherein the NDRG1-ERG fusion molecule being detected is a fusion mRNA molecule comprising a 5' portion of an NDRG1 mRNA and a '3 portion of an ERG mRNA, wherein the NDRG1-ERG fusion molecule is detected by using a hybridization method selected from the group consisting of in situ hybridization, hybridization to a microarray, solution phase hybridization, and Northern blot hybridization wherein the hybridization method is performed using an oligonucleotide probe specific for the junction of said fusion mRNA, wherein said junction comprises the sequence as set forth in SEQ ID NO: 4 or 5.

15. The method of claims 1, 6, or 14, wherein said sample is selected from the group consisting of prostate tissue, prostate cells, blood, urine, semen, and prostatic secretions.

\* \* \* \* \*